(12) United States Patent
Hattori et al.

(10) Patent No.: US 6,245,790 B1
(45) Date of Patent: Jun. 12, 2001

(54) OXAZOLE COMPOUNDS USEFUL AS PGE2 AGONISTS AND ANTAGONISTS

(75) Inventors: Kouji Hattori, Takarazuka; Osamu Okitsu, Tokyo; Naoaki Fujii, Takatsuki; Akira Tanaka, Takarazuka; Kiyoshi Taniguchi, Kobe; Satoshi Koyama, Nara; Mie Nishio, Himeji, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/424,253

(22) PCT Filed: Jun. 1, 1998

(86) PCT No.: PCT/JP98/02398

§ 371 Date: Mar. 8, 2000

§ 102(e) Date: Mar. 8, 2000

(87) PCT Pub. No.: WO98/55468

PCT Pub. Date: Dec. 10, 1998

(30) Foreign Application Priority Data

Jun. 2, 1997 (AU) ............................................ PO7132

(51) Int. Cl.$^7$ ............... A61K 31/426; C07D 263/46; C07D 277/38
(52) U.S. Cl. ............... 514/365; 514/374; 548/203; 548/204; 548/205; 548/235; 548/236
(58) Field of Search ............... 514/374, 365; 548/235, 236, 203, 204, 205

(56) References Cited

U.S. PATENT DOCUMENTS 5,100,889    3/1992   Misra et al. .
5,763,489    6/1998   Taniguchi et al. .
5,863,918    1/1999   Taniguchi et al. .
5,972,965  * 10/1999  Taniguchi et al. ................ 514/326

FOREIGN PATENT DOCUMENTS

WO 95/17393    6/1995   (WO) .
   95/24393  *  9/1995  (WO) .
WO 97/03973    2/1997   (WO) .

* cited by examiner

*Primary Examiner*—Joseph K. McKane
*Assistant Examiner*—Sonya N. Wright
(74) *Attorney, Agent, or Firm*—Oblon, Spivak, McClelland, Maier & Neustadt, P.C.

(57) ABSTRACT

Azole compounds of the formula:

wherein $R^1$ is lower alkyl substituted with carboxy, etc.,
$R^2$ is hydrogen or lower alkyl,
$R^3$ is aryl, etc.
$R^4$ is aryl, etc.
Q is

—CH$_2$— etc., and
X is O, NH or S,
and its salt, which are useful as medicament.

9 Claims, No Drawings

OXAZOLE COMPOUNDS USEFUL AS PGE2 AGONISTS AND ANTAGONISTS

This application is a 371 of PCT/JP98/02398 filed Jun. 1, 1998.

TECHNICAL FIELD

This invention relates to azole compounds and its salts which are useful as a medicament.

BACKGROUND ART

Some azole compounds are known, for example, in WO 95/17393, WO 95/24393 and WO 97/03973.

DISCLOSURE OF INVENTION

This invention relates to azole compounds. More particularly, this invention relates to azole compounds and its salts which are useful as prostaglandin $E_2$ (hereinafter described as $PGE_2$) agonist or antagonists.

Accordingly, one object of this invention is to provide new and useful azole compounds and its salts.

Another object of this invention is to provide processes for production of the azole compounds or its salts.

A further object of this invention is to provide a pharmaceutical composition containing, as an active ingredient, said azole compounds or its salts.

Still further object of this invention is to provide use of the azole compounds and its salts for manufacture of medicaments for treating or preventing $PGE_2$ mediated diseases.

The azole compounds of this invention can be represented by the following formula (I):

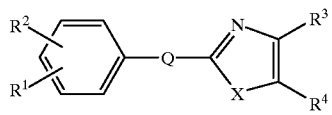

(I)

wherein $R^1$ is lower alkyl substituted with hydroxy, protected carboxy or carboxy; carboxy; protected carboxy; carbamoyl; a heterocyclic group; cyano; hydroxy; halo(lower)alkylsulfonyloxy; lower alkoxy optionally substituted with hydroxy or carbamoyl; aryl substituted with carboxy, protected carboxy, carbamoyl or a heterocyclic group; or amino optionally substituted with protected carboxy or lower alkylsulfonyl, $R^2$ is hydrogen or lower alkyl, $R^3$ is aryl optionally substituted with halogen, $R^4$ is aryl optionally substituted with halogen, Q is

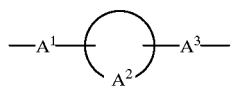

[in which —$A^1$— is a single bond or lower alkylene,

is cyclo($C_5$–$C_9$)alkene, cyclo($C_3$–$C_9$)alkane, bicyclo($C_6$–$C_9$)alkene or bicyclo($C_5$–$C_9$)alkane, and —$A^3$— is a single bond or lower alkylene], and X is O, NH or S.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies, and any form of the crystal of the compound (I).

According to the present invention, the azole compounds (I) or its salt can be prepared by the processes which are illustrated in the following scheme.

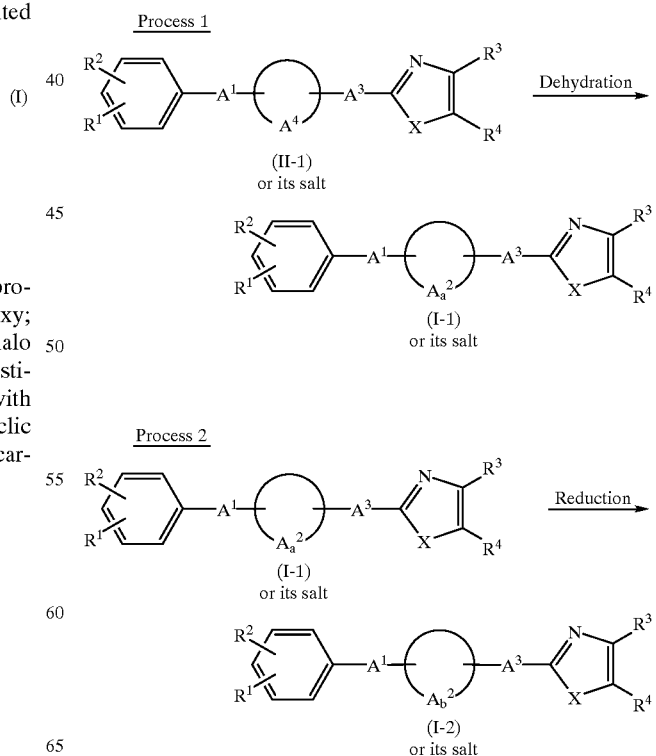

Process 3

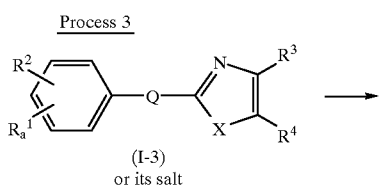

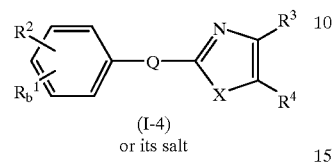

Process 4

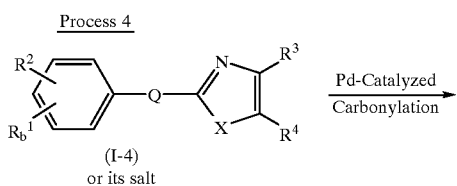

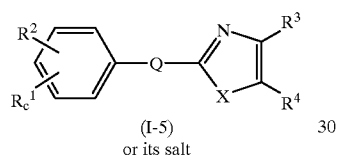

Process 5

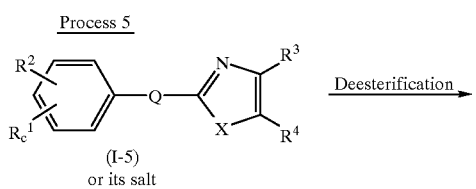

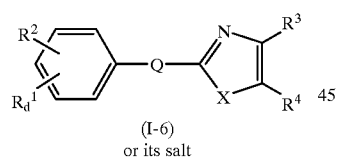

Process 6

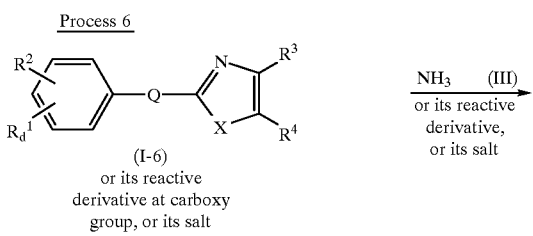

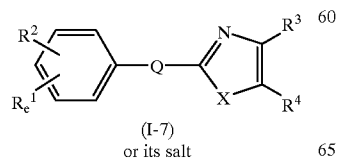

Process 7

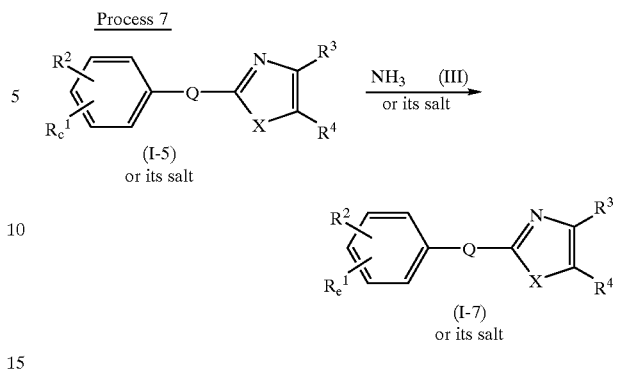

Process 8

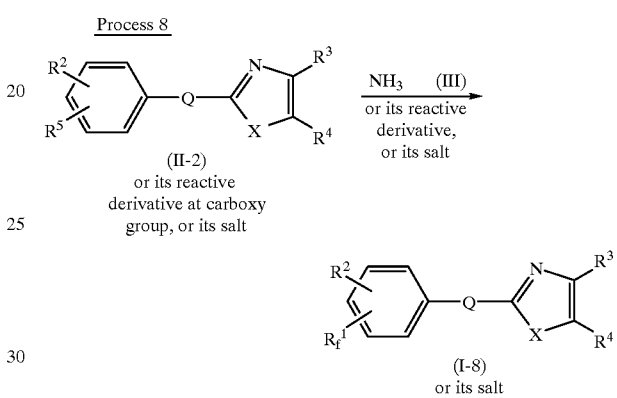

wherein $R^1$, $R^2$, $R^3$, $R^4_4$, —$A^1$—,

,

—$A^3$—, Q and X are each as defined above, $R_a^1$ is lower alkoxy, $R_b^1$ is halo(lower)alkylsulfonyloxy, $R_c^1$ is protected carboxy, $R_d^1$ is carboxy, $R_e^1$ is carbamoyl, $R_f^1$ is lower alkoxy substituted with carbamoyl, $R^5$ is lower alkoxy substituted with carboxy or protected carboxy,

is cyclo($C_5$–$C_9$)alkene or bicyclo($C_6$–$C_9$)alkene,

is cyclo($C_5$–$C_9$)alkane or bicyclo($C_6$–$C_9$)alkane, and

is cyclo($C_5$–$C_9$)alkane or bicyclo($C_6$–$C_9$)alkane, each of which is substituted with hydroxy.

The starting compounds (II-1) and (II-2) or their salts can be prepared according to a similar method described in WO 95/17393 or the following process.

Process A

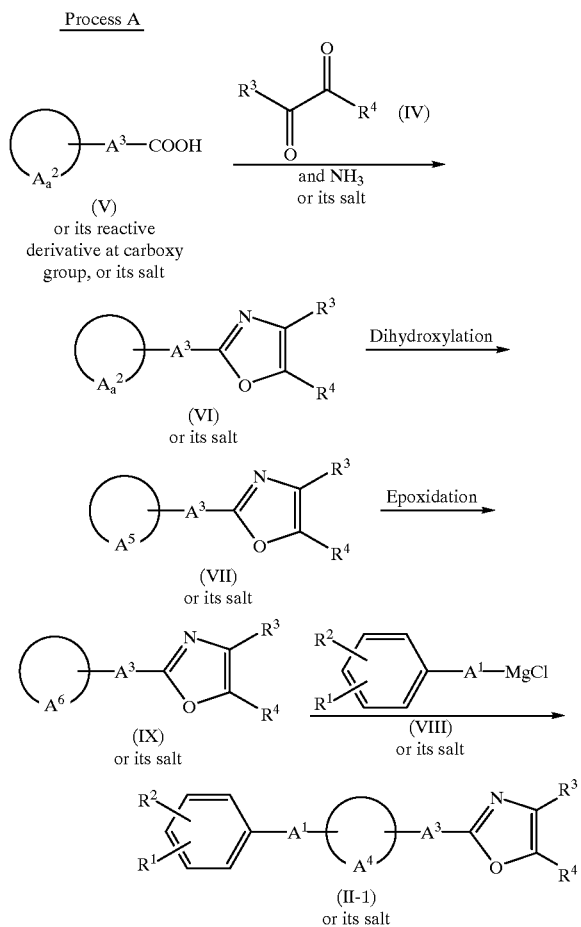

wherein $R^1$, $R^2$, $R^3$, $R^4$, —$A^1$—,

—$A^3$—,

and X are each as defined above, $R^5$ is hydrogen or lower alkyl,
$R^6$ is hydrogen or lower alkyl,

is cyclo($C_5$–$C_9$)alkane or bicyclo($C_6$–$C_9$)alkane, each of which has two hydroxy groups at adjacent carbon atoms, and

is cyclo($C_5$–$C_9$)alkane or bicyclo($C_6$–$C_9$)alkane, each of which has epoxy group at adjacent carbon atoms.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "lower alkyl" and lower alkyl moiety in the term "halo(lower)alkylsulfonyl" and "lower alkylsulfonyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "lower alkylene" may include straight or branched one having 1 to 6 carbon atom(s), such as methylene, ethylene, trimethylene, tetramethylene, pentamethylene and hexamethylene, preferably one having 1 to 3 carbon atom(s), more preferably methylene.

Suitable "cyclo($C_3$–$C_9$)alkane" may include cyclopropane, cyclopentane, cyclohexane, cycloheptane, cyclooctane, or the like preferably one having 5 to 7 carbon atoms.

Suitable "cyclo($C_5$–$C_9$)alkene" may include cyclopentene, cyclohexene, cycloheptene, cyclooctene, or the like, preferably one having 5 to 7 carbon atoms.

Suitable "bicyclo($C_5$–$C_9$)alkane" may include bicycloheptane (e.g., bicyclo[2.2.1]heptane, etc.), bicyclooctene (e.g., bicyclo[3.2.1]octane, etc.), or the like.

Suitable "bicyclo($C_6$–$C_9$)alkene" may include bicycloheptene (e.g., bicyclo[2.2.1.]hept-2-ene, etc.), bicyclooctene (e.g., bicyclo[3.2.1]oct-2-ene, etc.), or the like.

Suitable "aryl" may include phenyl, lower alkylphenyl (e.g., tolyl, ethylphenyl, propylphenyl, etc.), naphthyl or the like.

Suitable "heterocyclic group" may include one containing at least one hetero atom selected from nitrogen, sulfur and oxygen atom, and may include saturated or unsaturated, monocyclic or polycyclic group, and preferable one may be heterocyclic group such as 3 to 6-membered heteromonocyclic group containing 1 to 4 nitrogen atoms, for example, pyrrolyl, pyrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), or the like, more preferably tetrazolyl.

Suitable "lower alkoxy" may include methoxy, ethoxy propoxy, isopropoxy, butoxy, isobutoxy, t-butoxy, pentyloxy, t-pentyloxy, hexyloxy, or the like preferably methoxy.

Suitable "protected carboxy" may include esterified carboxy or the like.

Suitable example of the ester moiety of an esterified carboxy may be the ones such as lower alkyl (e.g., methyl, ethyl, propyl, isopropyl, butyl, isobutyl, tert-butyl, pentyl, hexyl, etc.) which may have at least one suitable substituent(s), for example, lower alkanoyloxy(lower)alkyl [e.g., acetoxymethyl, butyryloxymethyl, valeryloxymethyl, pivaloyloxymethyl, etc.], halo(lower)alkyl (e.g., 2-iodoethyl, 2,2,2-trichloroethyl, etc.); lower alkenyl (e.g., vinyl, allyl, etc.); lower alkynyl (e.g., ethynyl, propynyl, etc.); ar(lower)alkyl which may have at least one suitable substituent(s) (e.g., benzyl, 4-methoxybenzyl, 4-nitrobenzyl, phenethyl, trityl, etc.); aryl which may have at least one suitable substituent(s) (e.g., phenyl, tolyl, 4-chlorophenyl, tert-butylphenyl, xylyl, mesityl, cumenyl, etc.); phthalidyl; or the like.

Suitable "halo" group in the term of "halo(lower)alkylsulfonyl" may include fluoro, chloro, bromo, iodo, or the like.

Suitable "halo(lower)alkylsulfonyloxy" may include trifluoromethanesulfonyloxy, or the like.

Preferred embodiments of the azole compounds (I) are as follows:

$R^1$ is lower alkyl substituted with carboxy; carboxy; protected carboxy; carbamoyl; a heterocyclic group; lower alkoxy substituted with carbamoyl; aryl substituted with carboxy, carbamoyl or a heterocyclic group; or amino optionally substituted with lower alkylsulfonyl (more preferably lower alkyl substituted with carboxy; carboxy; carbamoyl; tetrazolyl; lower alkoxy substituted with carbamoyl; aryl substituted with carboxy or carbamoyl), $R^2$ is hydrogen or lower alkyl, Q is

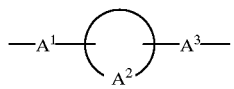

[in which —$A^1$— is a single bond or lower alkylene (more preferably methylene),

is cyclo($C_5$–$C_9$)alkene, cyclo($C_3$–$C_9$)alkane or bicyclo($C_6$–$C_9$)alkene, bicyclo($C_5$–$C_9$)alkane (more preferably cyclo($C_5$–$C_7$)alkene, cyclo($C_5$–$C_7$)alkane, bicyclo[2.2.1]heptane or bicyclo[2.2.1]heptane), and —$A^3$— is a single bond or lower alkylene (more preferably single bond)], and X is O.

The processes for preparing the object and starting compounds of the present invention are explained in detail in the following.

Process 1

The compound (I-1) or its salt can be prepared by subjecting the compound (II-1) or its salt to dehydrating reaction.

Suitable dehydrating reagent to be used in this reaction is, for example, an organic acid, such as toluenesulfonic acid (e.g., p-toluenesulfonic acid, etc.) and so on, and an inorganic acid such as hydrochlolic acd, sulfuric acid and so on.

This reaction is usually carried out in a solvent such as toluene, acetonitrile, benzene, N,N-dimethylformamide, tetrahydrofuran, methylene chloride, ethylene chloride, chloroform or any other solvent which does not adversely affect the reaction.

The reaction temperature is not critical and the reaction is usually carried out under cooling to warming.

Process 2

The compound (I-2) or its salt can be prepared by subjecting the compound (I-1) or its salt to reduction.

The present reduction is carried out by chemical reduction, catalytic reduction, or the like.

Suitable reducing agents to be used in chemical reduction are a combination of metal [e.g., tin, zinc, iron, etc.] or metallic compound [e.g., chromium chloride, chromium acetate, etc.] and an organic or inorganic acid [e.g., formic acid, acetic acid, propionic acid, trifluoroacetic acid, p-toluenesulfonic acid, hydrochloric acid, hydrobromic acid, etc.], or the like.

Suitable catalysts to be used in catalytic reduction are conventional ones such as platinum catalyst [e.g., platinum, platinum black, platinum oxide, etc.], palladium catalyst [e.g., palladium black, palladium oxide, palladium on carbon, etc.], nickel catalyst [e.g., reduced nickel, nickel oxide, Raney nickel, etc.], cobalt catalyst [e.g., reduced cobalt, Raney cobalt, etc.], iron catalyst [e.g., reduced iron, Raney iron, etc.], copper catalyst [e.g., reduced copper, Raney copper, Ullman copper, etc.] or the like.

The reduction is usually carried out in a conventional solvent which does not adversely influence the reaction such as water, an alcohol [e.g., methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming. Process 3

The compound (I-4) or its salt can be prepared from the compound (I-3) or its salt by subjecting to (i) the cleavage of ether bond of lower alkoxy group followed by (ii) halo-(lower)alkylsulfonylation reaction.

(i) Cleavage of Ether Bond

The cleavage of ether bond is carried out in the presence of an acid including the Lewis acid (e.g., hydrochloric acid, hydrobromic acid, hydroiodic acid, borontribromide, etc.), tri(lower)alkylsilyl iodide, (e.g., trimethylsilyl iodide, etc.) or any other reagent ordinary employed in the field of organic synthesis.

This reaction is usually carried out in a solvent such as toluene, acetonitrile, benzene, N,N-dimethylformamide, tetrahydrofuran, methylene chloride, ethylene chloride, chloroform or any other solvent which does not adversely affect the reaction.

The reaction temperature is not critical and the reaction is usually carried out under cooling to warming.

(ii) Halo(lower)alkylsulfonylation

Suitable reagent to be used in the halo(lower)alkylsulfonylation is, for example, halo(lower)alkylsulfonyl chloride, halo(lower)alkylsulfonic anhydride (e.g., trifluoromethanesulfonic anhydride, etc.) or the like. This reaction is preferably carried out in the presence of base.

Suitable base may include the inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.) or the like, and the organic base such as tri(lower)alkylamino (e.g., trimethylamine, diisopropylethylamine, etc.), pyridine or the like.

This reaction is usually carried out in a solvent such as toluene, acetonitrile, benzene, N,N-dimethylformamide, tetrahydrofuran, methylene chloride, ethylene chloride, chloroform or any other solvent which does not adversely affect the reaction.

The reaction temperature is not critical and the reaction is usually carried out under cooling to warming.

Process 4

The compound (I-5) or its salt can be prepared by reacting the compound (I-4) or its salt with carbon monoxide in the presence of catalytic amount of Palladium-catalyst and base.

Suitable Palladium-catalyst may be Palladium(II) acetate, Palladium(II) chloride, or the like.

Suitable base may include the inorganic base such as alkali metal hydroxide (e.g., sodium hydroxide, potassium hydroxide, etc.), alkaline earth metal hydroxide (e.g., calcium hydroxide, etc.), alkali metal carbonate (e.g., sodium carbonate, potassium carbonate, etc.), alkaline earth metal carbonate (e.g., magnesium carbonate, calcium carbonate, etc.) or the like, and the organic base such as tri(lower)alkylamino (e.g., trimethylamine, diisopropylethylamine, etc.), pyridine or the like.

This reaction can be preferably carried out in the presence of a ligand, such as tri(lower)alkylphosphin (e.g., trimethylphosphine, triethylphosphine, etc.), triarylphosphine (e.g., triphenylphosphine, etc.), bis(diarylphosphino) alkane (e.g., 1,3-bis(diphenylphosphino)-propane, or the like.

This reaction is usually carried out in a solvent such as toluene, acetonitrile, benzene, N,N-dimethylformamide, tetrahydrofuran, dimethylsulfoxide, methylene chloride, ethylene chloride, chloroform or any other solvent which does not adversely affect the reaction.

The reaction temperature is not critical and the reaction is usually carried out under cooling to warming.

Process5

The compound (I-6) or its salt can be prepared by subjecting the compound (I-5) or its salt to deesterification.

Suitable method of this reaction may include conventional one such as hydrolysis, reduction or the like.

(i) For Hydrolysis:

The hydrolysis is preferably carried out in the presence of a base or an acid including Lewis acid.

Suitable base may include an inorganic base and an organic base such as an alkali metal [e.g., sodium, potassium, etc.], the hydroxide or carbonate or bicarbonate thereof, or the like.

Suitable acid may include an organic acid [e.g., formic acid, acetic acid, trichloroacetic acid, trifluoroacetic acid, etc.] and an inorganic acid [e.g., hydrochloric acid, hydrobromic acid, sulfuric acid, hydrogen chloride, hydrogen bromide, etc.]. The deesterification using Lewis acid such as trihaloacetic acid [e.g., trichloroacetic acid, trifluoroacetic acid, etc.] or the like is preferably carried out in the presence of cation trapping agents [e.g., anisole, phenol, etc.].

The reaction is usually carried out in a solvent such as water, an alcohol [e.g., methanol, ethanol, etc.], methylene chloride, tetrahydrofuran, 1,2-dimethoxyethane, a mixture thereof or any other solvent which does not adversely influence the reaction. A liquid base or acid can be also used as the solvent. The reaction temperature is not critical and the reaction is usually carried out under cooling to warming.

(ii) For Reduction:

Reduction is carried out in a conventional manner, including chemical reduction and catalytic reduction.

Suitable reducing agents to be used in chemical reduction are a combination of a metal (e.g., tin, zinc, iron, etc.) or metallic compound (e.g., chromium chloride, chromium acetate, etc.) and an organic or inorganic acid (e.g., formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, colloidal palladium, palladium on barium sulfate, palladium on barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron, Raney iron, etc.), copper catalysts (e.g., reduced copper, Raney copper, Ullman copper, etc.) or the like. The reduction is usually carried out in a conventional solvent which does not adversely influence the reaction such as water, methanol, ethanol, propanol, ethyl acetate, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 6

The compound (I-7) or its salt can be prepared by reacting the compound (I-6) or its reactive derivative at the carboxy group, or its salt, with the compound (III) or its reactive derivative, or its salt.

Suitable reactive derivative of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silylating reagent such as N,O-bis (trimethylsilyl)acetamide, N-trimethylsilylacetamide, or the like.

Suitable reactive derivative of the compound (I-6) may include an acid chloride, an acid anhydride, an activated amide, an activated ester, or the like.

Suitable acid anhydride may be a symmetric anhydride or a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfuric acid, thiosulfuric acid, alkanesulfonic acid (e.g., methanesulfonic acid, ethanesulfonic acid, etc.), alkylcarbonic acid, aliphatic carboxylic acid (e.g., pivalic acid, pentanoic acid, isopentanoic acid, etc.); aromatic carboxylic acid (e.g., benzoic acid, chlorobenzoic acid, fluorobenzoic acid, nitrobenzoic acid, etc.), or the like.

Suitable activated amide may be imidazolylamide, 4-substituted imidazolylamide, dimethylpyrazolylamide, triazolylamide, tetrazolylamide, or the like.

Suitable activated ester may be dimethyliminomethyl $[(CH_3)_2N^+=CH—]$ ester, vinyl ester, propargyl ester, 4-nitrophenyl ester, 2,4-dinitrophenyl ester, trichlorophenyl ester, pentachlorophenyl ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an activated ester with a N-hydroxy compound (e.g., N,N-dimethylhydroxylamine, 1-hydroxy-2H-pyridone, N-hydroxysuccinimido, N-hydroxybenzotriazole, N-hydroxyphthalimide, etc.), or the like.

These reactive derivatives can optionally be selected from them according to the kind of compound (I-6) to be used.

When the compound (I-6) is used in free acid form or its salt form in the reaction, the reaction is preferably carried out in the presence of condensing agent.

Suitable condensing agent may include a carbodiimide (e.g., N,N'-dicyclohexylcarbodiimido, N-cyclohexyl-N'-(4-diethylaminocyclohexyl)carbodiimido, N-ethyl-N'-(3-dimethylaminopropyl)carbodiimido or its hydrochloride) diphenylphosphinic azido, diphenylphosphinic chloride, diethylphosphoryl cyanide, bis(2-oxo-3-oxazolidinyl)-phosphinic chloride, N,N'-carbonyldiimidazole, 2-ethoxy-1-ethoxycarbonyl-1,2-dihydroquinoline, cyanuric chloride, or the like.

The reaction may be also carried out in the presence of organic or inorganic base such as alkali metal carbonate, tri(lower) alkylamine, pyridine, N-(lower)alkylmorphorine, or the like.

The reaction is usually carried out in a conventional solvent such as water, acetone, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

Process 7

The compound (I-7) or its salt can be prepared by reacting the compound (I-5) or its salt with the compound (III) or its salt.

The reaction is usually carried out in a conventional solvent such as water, alcohol (e.g., methanol, ethanol, isopropyl alcohol, etc.), tetrahydrofuran, dioxane, methylene dichloride, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

Process 8

The compound (I-8) or its salt can be prepared by reacting the compound (II-2) or its reactive derivative at the carboxy group, or its salt, with the compound (III) or its reactive derivative, or its salt.

This reaction can be carried out in a similar manner to that of Process 6 or Process 7, and therefore the reagents to be used and the reaction conditions (e.g., solvent, reaction temperature, etc.) can be referred to those of the Process 6 and Process 7.

Process A

The compound (II-1) or (II-2), or its salt, can be prepared from the compound (V) or its salt according to the methods disclosed in the Preparation 1 to 7 or similar manners thereto.

Suitable salts of the object compound (I) and the compounds (II) to (IX) are pharmaceutically acceptable conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, etc.), an organic acid salt (e.g., acetate, maleate, tartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), or the like.

$PGE_2$ is known as one of the metabolites in an arachidonate cascade. And it is also known that it has various activities such as pain inducing activity, inflammatory activity, uterine contractile activity, a promoting effect on digestive peristalsis, an awaking activity, a suppressive effect on gastric acid secretion, hypotensive activity, blood platelet inhibition activity, bone-resorbing activity, angiogenic activity, or the like.

$PGE_2$-sensitive receptors have been sub-divided into four subtypes, EP1, EP2, EP3 and EP4, and these receptors have a wide distribution in various tissues. The effects associated with EP1 and EP3 receptors may be considered as excitatory, and are believed to be mediated by stimulation of phosphatidylinositol turnover or inhibition of adenyl cyclase activity, with resulting decrease in intracellular levels of cyclic AMP. In contrast, the effects associated with EP2 and EP4 receptors may be considered as inhibitory, and are believed to be associated with a stimulation of adenyl cyclase and an increase in levels of intracellular cyclic AMP. Especially, EP4 receptor may be considered to be associated with smooth muscle relaxation, anti-inflammatory or pro-inflammatory activities, lymphocyte differentiation, anti-allergic activities, mesangial cell relaxation or proliferation, gastric or enteric mucus secretion, or the like.

The azole compounds represented by the formula (I) or its salts possess binding activities to $PGE_2$-sensitive receptors, specifically to EP4 receptor, therefore they possess a $PGE_2$-antagonizing or $PGE_2$-inhibiting activity.

Therefore, the compounds represented by the formula (I) or its salts are useful for preventing or treating a $PGE_2$ mediated diseases, especially a EP4 receptors-mediated diseases, such as inflammatory conditions, various pains, or the like in human beings or animals.

More particularly, the compounds represented by formula (I) and its salt are useful for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atopic gastritis, gastritis varialoforme, ulcerative colitis, coeliac disease, regional ileitis, irritable bowel syndrome, etc:), gingivitis, inflammation, pain and tumescence after operation or injury, pyrexia, pain and other conditions associated with inflammation, allergic disease, systemic lupus erythematosus, scleroderma, polymyositis, tendinitis, bursitis, periarteritis nodose, rheumatic fever, Sjogren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc), liver dysfunction (hepatitis, cirrhosis, etc.), gastrointestinal dysfunction (diarrhea, inflammatory bowel diseases, etc.) shock, bone disease characterized by abnormal bone metabolism such as osteoporosis (especially, postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cachexia, calculosis, lithiasis (especially, urolithiasis), solid caricinoma, or the like in human being or animal.

In order to show the utility of the object compound (I), pharmacological data of the representative compounds thereof are shown in the following.

Binding Assay Using Expression of Prostanoide Receptor Subtype

[I] Test Compound:
(1) (S)-2-(4,5-Diphenyloxazol-2-yl)-1-(3-methoxybenzyl)-2-cyclopentene
(2) (S)-4-{[2-(4,5-Diphenyloxazol-2-yl)-2-cyclohexen-1-yl]- methyl}benzoic acid
(3) (S)-{3-{[2-(4,5-Diphenyloxazol-2-yl)-2-cyclohexen-1-yl]-methyl}phenoxy}actamide

[II] Test Method:

The membrane fraction was prepared using COS-7 cells transfected prostanoide receptor subtype (human EP4).

The Standard assay mixture contained membrane fraction, $[^3H]$-$PGE_2$ in final volume of 0.25 ml was incubated for 1 hour at 30° C. The reaction was terminated by that the mixture was rapidly filtered through a glass filter (GF/B). Then the filter was washed by 4 ml of ice-cold buffer at two times. The radioactivity associated with the filter was measured by liquid scintillation counting.

In the experiment for competition of specific $[^3H]$-$PGE_2$ was added at a concentration of 10 $\mu$M. The following buffer was used in all reactions.

Buffer: 20 mM Mes (pH 6.0), 1 mM EDTA, 10 mM $MgCl_2$

The inhibition (%) of each compound at a concentration of 10 $\mu$M was shown in Table. [III] Test Result:

| Test Compound | Inhibition (%) |
| --- | --- |
| (1) (10 $\mu$M) | >80 |
| (2) (10 $\mu$M) | >80 |
| (3) (10 $\mu$M) | >80 |

Effect on IgE and $IgG_1$ Secretion in Mouse B Lymphocytes

[I] Test Compound
Sodium (S)-3-{[2-(4,5-diphenyloxazol-2-yl)-2-cyclohexen-1-yl]methyl}benzoate

[II] Test Method

Inhibitory properties of a test compound against $PGE_2$-induced IgE and $IgG_1$ secretion in isolated resting B lymphocytes of mice were tested. Resting mouse B lymphocytes were isolated from spleens of 12-week-old $BDF_1$ male mice (Clea Japan Inc.) using adherent cell depletion, negative selection by FITC-anti-Thy 1.2 (30H12), FITC-anti–CD4 (GK1.5), FITC-anti–CD11b (M1/70) and FITC-anti–CD8a (5.–6.7) (Pharmingen) with anti-FITC Ab coating magnetic beads (PerSpective Daiagnostics) and Percoll gradient (Pharmacia). Resting B lymphocytes were cultured in flat-bottomed 96-well microtiter plates (Becton Dickinson) at $1\times10^6$ cells per ml and preincubated with a test compound or DMSO control for 30 minutes. Then $PGE_2$ were added at $10^{-6}$ M. After 1 hour, LPS and IL-4 were added and incubated at 37° C. in a humidified atmosphere with 5% $CO_2$. After 6 days, supernatants were collected and IgE and $IgG_1$ were measured by the ELISA.

[III] Test Result

|  | $-PGE_2$ | $+ 10^{-6}$ M $PGE_2$ |
| --- | --- | --- |
| IgE secretion (ng/ml) | | |
| Control | 27.6 ± 9.9 | 136.9 ± 22.2 # |
| + $10^{-5}$ M Test Compound | 21.2 ± 5.7 | 37.0 ± 7.0 * |
| $IgG_1$ secretion (ng./ml) | | |
| Control | 680.1 ± 37.9 | 1970.7 ± 117.5 # |
| + $10^{-5}$ M Test Compound | 1053.0 ± 176.2 | 1607.6 ± 150.9 # |

Data: Mean ± S.E.M. (n = 4)
$p < 0.01$ v.s. Control ($-PGE_2$)
* $p < 0.01$ v.s. Control ($+10^{-6}$ M $PGE_2$) (Dunett)

The pharmaceutical composition of the present invention can be used in the form of a pharmaceutical preparation, for example, in solid, semisolid or liquid form (e.g., tablet, pellet, troche, capsule, suppository, cream, ointment, aerosol, powder, solution, emulsion, suspension etc.), which contains the object compound (I) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyleneglycol, sucrose, starch, etc.), disintegrator (e.g., starch, carboxymethyl cellulose, calcium salt of carboxymethyl cellulose, hydroxypropylstarch, sodium glycol-starch, sodium bicarbonate, calcium phosphate, calcium citrate, etc.), lubricant (e.g., magnesium stearate, talc, sodium laurylsulfate, etc.), flavoring agent (e.g., citric acid, mentol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water), base wax (e.g., cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The patents, patent applications and publications cited herein are incorporated by referance.

Abbreviations used in this application are as follows:

| | |
| --- | --- |
| THF: | Tetrahydrofuran |
| EtOAc: | Ethyl acetate |
| $Et_2O$: | Diethyl ether |
| DMF: | N,N-Dimethylformamide |
| EtOH: | Ethyl alcohol |
| MeOH: | Methyl alcohol |
| AcOH: | Acetic acid |
| nBuli: | n-Butyllithium |
| MsCl: | Methanesulfonyl chloride |

| | |
|---|---|
| pTsOH: | p-Toluenesulfonic acid |
| AcONH₄: | Ammnonium acetate |
| DMAP: | Dimethylaminopyridine |
| Pd/C: | Palladium on carbone |
| Pd(OH)₂/C: | Palladium hydroxide on carbone |

The following Preparations and Examples are given only for the purpose of illustrating the present invention in more detail.

PREPARATION 1

To a solution of 1-cyclohexene-1-carboxylic acid (100 g) in $CH_2Cl_2$ (800 ml) was added $SOCl_2$ (117 ml) at room temperature. After being stirred for 4 hours, the solvent was evaporated in vacuo. The residue was diluted with $CH_2-C_2$ (1 l) and benzoin (170 g) and triethylamine (166 ml), and dimethylaminopyridine (10 g) were added to the solution at 0° C. under $N_2$. After being stirred for 4 hours at room temperature, the solvent was evaporated in vacuo, and the residue was partitioned between ethyl acetate and water. The organic layer was washed with 1N-HCl solution, sat. $NaHCO_3$, and brine, dried over $MgSO_4$, and evaporated in vacuo. The obtained compound and $AcONH_4$ (200 g) were dissolved in acetic acid (1500 ml) and the mixture was stirred for 4 hours at 100° C. After the solvent was removed, the residue was partitioned between ethyl acetate and water. The organic layer was washed with water, sat. $NaHCO_3$ and brine. The dried solvent was evaporated in vacuo and the residue was purified by chromatography on silica gel to give 1-(4,5-diphenyloxazol-2-yl)-1-cyclohexene (171 g).

NMR ($CDCl_3$, $\delta$): 1.6–1.9 (4H, m), 2.2–2.4 (2H, m), 2.5–2.7 (2H, m), 6.90 (1H, m), 7.2–7.8 (10H, m) Mass (m/z): 302(M+H)⁺.

PREPARATION 2

A solution of AD-mix-α® (30 g) in a mixture of t-BuOH (600 ml) and water (600 ml) was stirred for 1 hour, and then methanesulfonamide (9.3 g) and 1-(4,5-diphenyloxazol-2-yl)-1-cyclohexene added to the solution at room temperature. After being stirred for 20 hours at the same temperature, sodium sulfite (60 g) was added, and the mixture was stirred for 30 minutes. The mixture was partitioned between ethyl acetate and water. The organic layer was washed with 1N-HCl solution, sat. $NaHCO_3$ and brine, dried over $MgSO_4$ and evaporated in vacuo. The residue was purified by chromatography on silica gel to afford (1R,2S)-1,2-dihydroxy-1-(4,5-diphenyloxazol-2-yl)cyclohexane (30 g).

IR (neat): 3400, 3200, 1460 cm⁻¹ ; NMR ($CDCl_3$, $\delta$): 1.2–1.9 (7H, m), 2.2–2.4 (1H, m), 3.34 (1H, s), 3.70 (1H, br s), 4.1–4.4 (1H, m), 7.2–7.8 (10H, m); Mass (m/z): 365 (M+H)⁺.

PREPARATION 3

The following compound was obtained according to a similar manner to that of Preparation 2.
(1) (1S,2R)-1,2-Dihydroxy-1-(4,5-diphenyloxazol-2-yl)-cyclohexane IR (neat): 3400, 3200, 1460 cm⁻¹; NMR ($CDCl_3$, $\delta$): 1.2–1.9 (7H, m), 2.2–2.4 (1H, m), 3.34 (1H, s), 3.70 (1H, br s), 4.1–4.4 (1H, m), 7.2–7.8 (10H, m); Mass (m/z): 365 (M+H)⁺.

PREPARATION 4

To a solution of (1R,2S)-1,2-dihydroxy-1-(4,5-diphenyl-oxazol-2-yl)cyclohexane (18 g) in $CH_2Cl_2$ (200 ml) were added orthoacetic acid trimethyl ester (9.7 ml) and p-toluenesulfonic acid (20 mg) at room temperature under $N_2$. After being stirred for 30 minutes, the solvent was evaporated in vacuo. The residue was diluted with $CH_2Cl_2$ (200 ml) and acetylbromide (5.8 ml) was added to the solution at 0° C. under $N_2$. After being stirred for 2 hours at room temperature, the solvent was evaporated in vacuo, the residue was diluted with MeOH (200 ml), and $K_2CO_3$ (12 g) was added to the solution at room temperature. The mixture was stirred for 2 hours at the same temperature and partitioned between ethyl acetate and water. The organic layer was washed with 1N-HCl, water, sat. $NaHCO_3$ and brine. The dried solvent was evaporated in vacuo and the residue was purified by chromatography on silica gel to give (1R, 2S)-1-(4,5-diphenyl-oxazol-2-yl)-1,2-epoxycyclohexane (14.1 g).

NMR ($CDCl_3$, $\delta$): 1.2–1.8 (4H, m), 1.9–2.2 (2H, m), 2.2–2.4 (1H, m), 2.6–2.8 (1H, m), 3.83 (1H, m), 7.2–7.6 (10H, m); Mass (m/z): 318 (M+H)⁺.

PREPARATION 5

The following compound was obtained according to a similar manner to that of Preparation 4.
(1S,2R)-1-(4,5-Diphenyloxazol-2-yl)-1,2-epoxycyclohexane NMR ($CDCl_3$, $\delta$): 1.2–1.8 (4H, m), 1.9–2.2 (2H, m), 2.2–2.4 (1H, m), 2.6–2.8 (1H, m), 3.83 (1H, m), 7.2–7.6 (10H, m); Mass (m/z): 318 (M+H)⁺.

PREPARATION 6

To a solution of (1R,2S)-1-(4,5-diphenyloxazol-2-yl)-1,2-epoxycyclohexane (20 g) and CuBr (3.0 g) in tetrahydrofuran (400 ml) was dropwise added a solution of 3-methoxybenzylmagnesium chloride [prepared from 3-methoxy-benzylchloride (50 g) and Mg (9.2 g)] in tetrahydrofuran (500 ml) at −78° C. under $N_2$. The mixture was stirred for 2 hours at the room temperature and partitioned between ethyl acetate and water. The organic layer was washed with 1N-HCl, water, sat. $NaHCO_3$ and brine. The dried solvent was evaporated in vacuo and the residue was purified by chromatography on silica gel to give (1R,2S)-1-(4,5-diphenyloxazol-2-yl)-1-hydroxy-2-(3-methoxybenzyl)cyclohexane (29.2 g).

IR (Nujol): 3400, 1600 cm⁻¹; NMR ($CDCl_3$, $\delta$): 1.4–2.4 (9H, m), 3.07 (1H, d, J=10 Hz), 3.52 (1H, m), 3.74 (3H, s), 6.7–6.9 (4H, m), 7.15 (1H, t, J=8 Hz), 7.2–7.8 (10H, m);
Mass (m/z): 440 (M+H)⁺.

PREPARATION 7

The following compound was obtained according to a similar manner to that of Preparation 6.
(1S,2R)-1-(4,5-Diphenyloxazol-2-yl)-1-hydroxy-2-(3-methoxybenzyl)cyclohexane

PREPARATION 8

To a solution of diisopropylamine (1.44 ml) in THF (8 ml) was added n-BuLi (1.56M solution in hexane, 70 ml) at −60° C. The mixture was warmed to 0° C., stirred for 10 minutes, and recooled to −60° C. To the mixture was added cyclohexanone (0.98 g) in THF (5 ml). After stirring for 1 hour, 3-methoxy-2-methylbenzaldehyde (1.5 g) was added and the mixture was stirred for 1.5 hours at the same temperature. The reaction mixture was quenched with saturated $NH_4Cl$ solution, warmed to room temperature, extracted with EtOAc. The organic layer was washed with water and brine, dried over magnesium sulfate, evaporated in vacuo. The residue was purified by silica gel column chromatography (hexane-EtOAc 4:1 to 2:1) to give 2-[hydroxy-(3-methoxy-2-methylphenyl)methyl]cyclohexanone (1.86 g) as an oil.

IR (neat): 3504, 2941, 2862, 1699, 1585, 1468, 1257 cm$^{-1}$ Mass (m/z): 231 (H+H–H$_2$O)$^+$.

PREPARATION 9

The following compounds described in (1) to (4) were obtained according to a similar manner to that of Preparation 8.

(1) 2-[Hydroxy-(3-methoxy-4-methylphenyl)methyl]cyclohexanone

IR (neat): 3502, 2939, 2862, 1699, 1612, 1585, 1508, 1466, 1452, 1412, 1255 cm$^{-1}$; Mass (m/z): 231 (M+H–H$_2$O)$^+$.

(2) 2-[Hydroxy-(3-methoxy-5-methylphenyl)methyl]cyclohexanone

IR (neat): 3508, 2839, 2862, 1699, 1597, 1464, 1325, 1292 cm$^{-1}$; Mass (m/z): 231 (M+H–H$_2$O)$^+$.

(3) 2-[Hydroxy-(5-methoxy-2-methylphenyl)methyl]cyclohexanone

IR (neat) 3508, 2939, 2862, 1697, 1610, 1581, 1500, 1450, 1300, 1248 cm$^{-1}$; Mass (m/z): 231 (M+H–H$_2$O)$^+$.

(4) 2-[Hydroxy-(2-methoxyphenyl)methyl]cyclohexanone

NMR (CDCl$_3$, δ): 1.20–2.90 (9H, m), 3.73–3.90 (3H, m), 5.23–5.70 (1H, m), 6.80–7.52 (4H, m) Mass (m/z): 217 (M+H–H$_2$O)$^+$.

PREPARATION 10

To a solution of 2-[hydroxy-(3-methoxy-2-methylphenyl)-methyl]cyclohexanone (1.85 g) in THF (20 ml) was added conc. HCl (0.5 ml) at 5° C. and the mixture was stirred at room temperature for 1 hour. The reaction mixture was diluted with EtOAc, washed with saturated sodium hydrogen carbonate, water, and brine, dried over magnesium sulfate, evaporated in vacuo. The residue was dissolved in MeOH (30 ml) and 10% Pd/C (wet) (400 mg) was added. The mixture was stirred under hydrogen atmosphere at room temperature for 2 hours. The catalyst was removed by filtration and the filtrate was evaporated. The residue was pufified by silica gel column chromatography (hexane-EtOAc 12:1 to 8:1) to give 2-(3-methoxy-2-methylbenzyl)cyclohexanone (980.6 mg) as an oil.

IR (neat): 2935, 2860, 1709, 1583, 1468, 1257, 1109 cm$^{-1}$ NMR (CDCl$_3$, δ): 1.20–2.58 (10H, m), 2.13 (3H, s), 3.22–3.34 (1H, m), 3.81 (3H, s), 6.69–6.77 (2H, m), 7.08 (1H, dd, J=7.8, 7.8 Hz)

PREPARATION 11

The following compounds described in (1) to (3) were obtained according to a similar manner to that of Preparation 10.

(1) 2-(3-Methoxy-4-methylbenzyl)cyclohexanone

IR (neat): 2937, 2860, 1711, 1612, 1583, 1510, 1450, 1414, 1257 cm$^{-1}$; NMR (CDCl$_3$, δ): 1.23–2.62 (10H, m), 2.17 (3H, s), 3.20 (1H, dd, J=13.5, 4.4 Hz), 3.81 (3H, s), 6.60–6.67 (2H, m), 7.02 (1H, d, J=7.4 Hz)

(2) 2-(3-Methoxy-5-methylbenzyl)cyclohexanone

IR (neat): 2935, 2860, 1711, 1610, 1595, 1462, 1296, 1151 cm$^{-1}$; NMR (CDCl$_3$, δ): 1.22–2.63 (10H, m), 2.30 (3H, s), 3.18 (1H, dd, J=13.7, 4.4 Hz), 3.77 (3H, s), 6.48–6.60 (3H, m); Mass (m/z): 233 (M+H)$^+$.

(3) 2-(5-Methoxy-2-methylbenzyl)cyclohexanone

IR (neat): 2935, 2862, 1709, 1610, 1579, 1502, 1448, 1309, 1288, 1254 cm$^{-1}$; NMR (CDCl$_3$, δ): 1.25–2.60 (10H, m), 2.20 (3H, s), 3.22 (1H, dd, J=13.5, 3.8 Hz), 3.77 (3H, s), 6.60–6.78 (2H, m), 7.00–7.10 (1H, m).

PREPARATION 12

A mixture of 2-[hydroxy-(2-methoxyphenyl)methyl]cyclohexanone (3.71 g), 10% Pd/C (wet) (1.0 g), and 20% Pd(OH)$_2$/C (180 mg) in MeOH-EtOAc (2:1, 150 ml) was stirred under hydrogen atmosphere at room temperature for 28 hours. The catalyst was removed by filtration and the filtrate was evaporated. The residue was purified by silica gel column chromatography (hexane-EtOAc 7:1) to give 2-(2-methoxybenzyl)cyclohexanone (2.65 g) as an oil.

IR (neat); 2935, 2860, 1709, 1601, 1587, 1495, 1464, 1244 cm$^{-1}$; NMR (CDCl$_3$, δ): 1.22–2.74 (10H, m), 3.22 (1H, dd, J=13.4, 4.6 Hz), 3.79 (3H, s), 6.76–6.92 (2H, m), 7.05–7.23 (2H, m); Mass (m/z): 219 (M+H)$^+$.

PREPARATION 13

To a mixture of (2-oxocyclohex-1-yl)acetic acid (5.6 g), benzoin (7.4 g), 4-dimethylaminopyridine (0.42 g) and dichloromethane (60 ml), 1-ethyl-3-(3'-dimethylaminopropyl)-carbodiimide hydrochloride (8.7 g) was added in ice-water bath. After the reaction mixture was raised to room temperature, N,N-dimethylformamide (10 ml) was added to dissolve benzoin and stirred overnight. After usual workup, 1,2-diphenyl-2-oxoethyl (2-oxocyclohex-1-yl)acetate (15.5 g) was obtained as a crude solid.

PREPARATION 14

A mixture of ammonium acetate (6.3 g), acetic acid (30 ml) and 1,2-diphenyl-2-oxoethyl (2-oxocyclohex-1-yl) acetate (15.0 g) was heated under reflux for 2.5 hours. After used workup, the crude product was purified by column chromatography (silica gel 100 g, eluent; hexane:ethyl acetate=20:1 then 9:1 then 6:1) to give 2-[(4,5-diphenyl-oxazol-2-yl)methyl]cyclohexanone as an amorphous solid.

IR (film): 2935, 1714, 1572, 1502, 1446, 1313, 1220, 1130, 1059, 962, 764, 696 cm$^{-1}$; NMR (CDCl$_3$, δ): 1.40–2.06 (4H, m), 2.10–2.57 (4H, m), 2.70 (1H, dd, J=8.2, 15.7 Hz), 2.98–3.28 (1H, m), 3.41 (1H, dd, J=7.1, 21.2 Hz), 7.30–7.41 (6H, m), 7.55–7.65 (4H, m); Mass (m/z): 332 (M+H)$^+$, 222.

EXAMPLE 1

A mixture of (1R,2S)-1-(4,5-diphenyloxazol-2-yl)-1-hydroxy-2-(3-methoxybenzyl)cyclohexane (28 g) and p-toluene-sulfonic acid (2.5 g) in toluene (300 ml) was stirred for 4 hours under reflux. The solution was washed with water, sat. NaHCO$_3$ and brine, dried over MgSO$_4$ and evaporated in vacuo. The residue was purified by chromatography on silica gel to afford (S)-2-(4,5-diphenyloxazol-2-yl)-1-(3-methoxybenzyl)-2-cyclohexene (16 g).

NMR (CDCl$_3$, δ): 1.4–1.9 (4H, m), 2.1–2.4 (2H, m), 2.53 (1H, dd, J=10.2, 12.8 Hz), 3.1–3.3 (1H, m), 3.31 (1H, dd, J=3.2, 12.8 Hz), 3.77 (3H, s), 6.80 (1H, 8 Hz), 6.9–7.0 (3H, m), 7.20 (1H, t, J=8 Hz), 7.2–7.8 (10H, m); Mass (m/z): 422 (M+H)$^+$.

EXAMPLE 2

The following compound was obtained according to a similar manner to that of Example 1.

(R)-2-(4,5-Diphenyloxazol-2-yl)-1-(3-methoxybenzyl)-2-cyclohexene

NMR (CDCl$_3$, δ): 1.4–1.9 (4H, m), 2.1–2.4 (2H, m), 2.53 (1H, dd, J=10.2, 12.8 Hz), 3.1–3.3 (1H, m), 3.31 (1H, dd, J=3.2, 12.8 Hz), 3.77 (3H, s), 6.80 (1H, 8 Hz), 6.9–7.0 (3H, m), 7.20 (1H, t, J=8Hz), 7.2–7.8 (10H, m); Mass (m/z): 422 (M+H)$^+$.

EXAMPLE 3

To a solution of (S)-2-(4,5-diphenyloxazol-2-yl)-1-(3-methoxybenzyl)-2-cyclohexene (8.5 g) in dichloromethane (100 ml) was added BBr$_3$ (50 ml, 1M solution in dichloromethane) at 0° C. After being stirred for 2 hours, the solvent was evaporated in vacuo. The residue was diluted with ethyl acetate, and the mixture was washed with water and brine. The dried solvent was evaporated in vacuo and dissolved in dichloromethane (50 ml). To the solution were added trifluoromethanesulfonic acid anhydride (5.0 ml) and 2,6-lutidine (6.2 ml) −78° C. After being stirred for 2 hours, the solvent was evaporated in vacuo. The residue was diluted with ethyl acetate, and the mixture was washed with water, sat. NaHCO$_3$ and brine. The dried solvent was evaporated in vacuo and the residue was purified by chromatography on silica gel to give (S)-3-{[2-(4,5-diphenyl-oxazol-2-yl)-2-cyclohexen-1-yl]methyl}phenyl trifluoromethanesulfonate (9.1 g).

IR (Nujol): 1600, 1520, 1480 cm$^{-1}$; NMR (CDCl$_3$, δ): 1.4–2.0 (4H, m), 2.2–2.4 (2H, m), 2.60 (1H, dd, J=10.4, 13.2 Hz), 3.0–3.2 (1H, m), 3.35 (1H, dd, J=4.0, 13.2 Hz), 6.9 (1H, m), 7.1–7.8 (14H, m); Mass (m/z): 540 (M+H)$^+$.

EXAMPLE 4

To a dichloromethane solution (30 ml) of 3-{[2-(4,5-diphenyloxazol-2-yl)-2-cyclopenten-1-yl]methyl}phenol (3.06 g), triethylamine (1.5 ml) and DMAP (a catalytic amount), was added trifluoroacetic anhydride (1.5 ml) for 5 minutes at −60° C. and overnight at room temperature. The solvent was evaporated in vacuo and residue was partitioned between ethyl acetate and 1N hydrochloric acid. The organic layer was washed with brine. After dried over MgSO$_4$, the solution was evaporated in vacuo. The residue was purified by silica gel chromatography to afford 3-{[2-(4,5-diphenyloxazol-2-yl)-2-cyclopenten-1-yl]methyl}phenyl trifluoromethanesulfonate (3.18 g).

NMR (CDCl$_3$, δ): 1.68–1.92 (1H, m), 2.00–2.20 (1H, m), 2.32–2.48 (2H, m), 2.75 (1H, dd, J=13.5, 9.0 Hz), 3.46 (1H, dd, J=3.9, 13.5 Hz), 3.54 (1H, m), 6.69 (1H, m), 7.08–7.16 (2H, m), 7.26–7.43 (8H, m), 7.60–7.72 (4H, m); Mass (m/z): 526 (M+H)$^+$.

EXAMPLE 5

The following compounds were obtained according to a similar manner to that of Example 3.
(1) (R)-3-{[2-(4,5-Diphenyloxazol-2-yl)-2-cyclohexen-1-yl]-methyl}phenyl trifluoromethanesulfonate
(2) (S)-3-{[2-(4,5-Diphenyloxazol-2-yl)-2-cyclopenten-1-yl]-methyl}phenyl trifluoromethanesulfonate IR (Nujol): 1600, 1580 cm$^{-1}$; NMR (CDCl$_3$, δ): 1.6–2.2 (2H, m), 2.4 (2H, m), 2.75 (1H, dd, J=9.0, 13.4 Hz), 3.44 (1H, dd, J=4.0, 13.4 Hz), 3.56 (1H, m), 6.70 (1H, m), 7.0–7.8 (14H, m); Mass (m/z): 526 (M+H)$^+$.

EXAMPLE 6

The following compound was obtained according to a similar manner to that of Example 4.
4-{[2-(4,5-Diphenyloxazol-2-yl)-2-cyclohexen-1-yl]-methyl}phenyl trifluoromethanesulfonate NMR (CDCl$_3$, δ): 1.4–2.0 (4H, m), 2.6–2.8 (1H, m), 3.0–3.2 (1H, m), 6.86 (1H, m), 7.0–7.5 (14H, m)

EXAMPLE 7

To a solution of (S)-3-{[2-(4,5-diphenyloxazol-2-yl)-2-cyclohexen-1-yl]methyl}phenyl trifluoromethanesulfonate (7 g) in a mixture of methanol (30 ml) and dimethylformamide (40 ml) were added 1,3-bis(diphenylphosphino) propane (1.1 mg), palladium acetate (0.58 mg), and triethylamine (5.4 ml). After being stirred for 5 hours at 80° C. under CO atmosphere, the mixture was partitioned between ethyl acetate and water and the organic layer was washed with 1N-HCl, sat. NaHCO$_3$, and brine. The dried solvent was evaporated in vacuo and the obtained solid was washed with ether to afford methyl (S)-3-{[2-(4,5-diphenyloxazol-2-yl)-2-cyclohexen-1-yl]methyl}-benzoate (4.2 g).

IR (Nujol): 1720 cm$^{-1}$; NMR (CDCl$_3$, δ): 1.4–2.0 (4H, m), 2.1–2.4 (2H, m), 2.62 (1H, dd, J=10.0, 13.0 Hz), 3.16 (1H, m), 3.33 (1H, dd, J=3.0, 13.0 Hz), 3.88 (3H, s), 6.92 (1H, t, J=4.0 Hz), 7.3–7.8 (12H, m), 7.85 (1H, d, J=8 Hz), 8.00 (1H, s); Mass (m/z): 450 (M+H)$^+$.

EXAMPLE 8

The following compounds were obtained according to a similar manner to that of Example 7.
(1) Methyl (R)-3-{[2-(4,5-diphenyloxazol-2-yl)-2-cyclohexen-1-yl]methyl}benzoate IR (Nujol): 1720 cm$^{-1}$; NMR (CDCl$_3$, δ): 1.4–2.0 (4H, m), 2.1–2.4 (2H, m), 2.62 (1H, dd, J=10.0, 13.0 Hz), 3.16 (1H, m), 3.33 (1H, dd, J=3.0, 13.0 Hz), 3.88 (3H, s), 6.92 (1H, t, J=4.0 Hz), 7.3–7.8 (12H, m), 7.85 (1H, d, J=8 Hz), 8.00 (1H, s); Mass (m/z): 450 (M+H)$^+$.
(2) Methyl 4-{[2-(4,5-diphenyloxazol-2-yl)-2-cyclohexen-1-yl]methyl}benzoate IR (Nujol): 1720 cm$^{-1}$; NMR (CDCl$_3$, δ): 1.4–2.0 (4H, m), 2.2–2.4 (2H, m), 2.63 (1H, dd, J=10.2, 13.0 Hz), 3.20 (1H, m), 3.39 (1H, dd, J=3.4, 13.0 Hz.), 3.89 (3H, s), 6.92 (1H, m), 7.2–7.8 (12H, m), 7.96 (2H, d, J=8 Hz); Mass (m/z): 450 (M+H)$^+$.
(3) Ethyl (S)-3-{[2-(4,5-diphenyloxazol-2-yl)-2-cyclopenten-1-yl]methyl}benzoate IR (Nujol): 1720 cm$^{-1}$; Mass (m/z): 450 (M+H)$^+$.

EXAMPLE 9

To a solution of methyl (S)-3-{[2-(4,5-diphenyloxazol-2-yl)-2-cyclohexen-1-yl]methyl}benzoate (0.3 g) in a mixture of ethanol (8 ml) and tetrahydrofuran (5 ml) was added 1N-NaOH solution (3.5 ml). After being stirred for 24 hours at the same temperature, the solvent was removed. The residue was partitioned between ethyl acetate and 1N-HCl and the organic layer was washed with brine. The dried solvent was evaporated in vacuo and the obtained solid was washed with a mixture hexane and ether to afford (S)-3-{[2-(4,5-diphenyl-oxazol-2-yl)-2-cyclohexen-1-yl] methyl}benzoic acid(O.28 g).

IR (Nujol): 1700 cm$^{-1}$; NMR (CDCl$_3$, δ): 1.4–1.9 (4H, m), 2.2–2.4 (2H, m), 2.65 (1H, dd, J=10.0, 13.0 Hz), 3.2 (1H, m), 3.35 (1H, dd, J=3.0, 13.0 Hz), 6.93 (1H, t, J=3.8 Hz), 7.2–7.8 (12H, m), 7.93 (1H, d, J=8 Hz), 8.10 (1H, s); Mass (m/z): 436 (M+H)$^+$.

EXAMPLE 10

The following compounds were obtained according to a similar manner to that of Example 9.
(1) (R)-3-{[2-(4,5-Diphenyloxazol-2-yl)-2-cyclohexen-1-yl]-methyl}benzoic acid IR (Nujol): 1700 cm$^{-1}$; NMR (CDCl$_3$, δ): 1.4–1.9 (4H, m), 2.2–2.4 (2H, m), 2.65 (1H, dd, J=10.0, 13.0 Hz), 3.2 (1H, m), 3.35 (1H, dd, J=3.0, 13.0 Hz), 6.93 (1H, t, J=3.8 Hz), 7.2–7.8 (12H, m), 7.93 (1H, d, J=8 Hz), 8.10 (1H, s); Mass (m/z): 436 (M+H)$^+$.

(2) 4-{[2-(4,5-Diphenyloxazol-2-yl)-2-cyclohexen-1-yl]-methyl}benzoic acid

IR (Nujol): 1690 cm$^{-1}$; NMR (CDCl$_3$, δ): 1.4–1.9 (4H, m), 2.2–2.4 (2H, m), 2.6–2.8 (1H, m), 3.2 (1H, m), 3.40 (1H, dd, J=3.2, 13.2 Hz), 6.93 (1H, m), 7.2–7.8 (12H, m), 8.03 (2H, d, J=8 Hz); Mass (m/z): 436 (M+H)$^+$.

(3) (S)-3-{[2-(4,5-Diphenyloxazol-2-yl)-2-cyclopenten-1-yl]methyl}benzoic acid

IR (Nujol): 1680 cm$^{-1}$; NMR (CDCl$_3$): 1.7–1.9 (1H, m), 2.0–2.2 (1H, m), 2.38–2.52 (2H, m), 2.74 (1H, dd, J=12.7, 9.1 Hz), 3.46 (1H, dd, J=12.7, 4.2 Hz), 3.60 (1H, m), 6.72 (1H, m), 7.2–7.7 (12H, m), 7.9–8.0 (2H, m). Mass (m/z): 422 (M+H)$^+$.

(4) 3-{[(1S,2S)-2-(4,5-Diphenyloxazol-2-yl)-1-cyclopentyl]-methyl}benzoic acid

IR (Nujol): 1680 cm$^{-1}$; NMR (CDCl$_3$, δ): 1.4–2.4 (6H, m), 2.4–2.8 (3H, m), 3.52 (1H, m), 7.2–7.4 (8H, m), 7.5–7.7 (4H, m), 7.8–8.0 (2H, m); Mass (m/z): 424 (M+H)$^+$.

(5) 3-{[(1S,2R)-2-(4,5-Diphenyloxazol-2-yl)-1-cyclopentyl]- methyl}benzoic acid Mass (m/z): 424 (M+H)$^+$.

IR (Nujol): 1680 cm$^{-1}$; NMR (CDCl$_3$, δ): 1.4–2.5 (6H, m), 2.5–3.1 (4H, m), 7.2- 7.8 (12H, m), 7.82 (1H, d, J=8Hz), 7.93 (1H, S); (6) 3-{[2-(4,5-Diphenyloxazol-2-yl)-1-cyclopenten-1-yl]- methyl1benzoic acid IR (Nujol): 1680 cm$^{-1}$ ; NMR (CDCl$_3$, δ): 1.7–2.0 (2H, m), 2.4–2.6 (2H, m), 2.9- 3.1 (2H, m), 4.21 (2H, s), 7.2–7.7 (1OH, m), 7.9- 8.1 (4H, m) ; Mass (m/z): 422 (M+H)$^+$.

EXAMPLE 11

A mixture of (S)-3-{[2-(4,5-diphenyloxazol-2-yl)-2-cyclohexen-1-yl]methyl}benzoic acid (0.1 g) and 10% Pd/C (0.1 g) in methanol (20 ml) was stirred under H$_2$ for 8 hours. The catalyst was filtered off and filtrate was evaporated in vacuo to give 3-{[(lS)-2-(4,5-diphenyloxazol-2-yl)-1-cyclohexyl]methyl}benzoic acid (0.1 g).

IR (neat): 3400, 1690 cm$^{-1}$ ; NMR (CDCl$_3$, δ): 1.2–2.5 (9H, m), 2.6–3.0 (2H, m), 3.25 -(1H, m), 7.2–8.1 (14H, m); Mass (m/z): 438 (M+H)$^+$.

EXAMPLE 12

The following compounds were obtained from ethyl (S)-3-{[2-(4,5-diphenyloxazol-2-yl)-2-cyclopenten-1-yl]-methyl}benzoate according to a similar manner to that of Example 11.
(1) Ethyl 3-{[(1S,2S)-2-(4,5-diphenyloxazol-2-yl)-1-cyclopentyl]methyl}benzoate
(2) Ethyl 3-{[(1S,2R)-2-(4,5-diphenyloxazol-2-yl)-1-cyclopentyl]methyl}benzoate

EXAMPLE 13

To a solution of (S)-3-{[2-(4,5-diphenyloxazol-2-yl)-2-cyclohexen-1-yl]methyl}benzoic acid (0.3 g) in a tetrahydrofuran (10 ml) were added isobutyl chloroformate (0.15 ml) and triethylamine (0.2 ml) at 0° C. under N$_2$. After being stirred for 30 minutes, NH$_3$ (5 ml, 4M solution in methanol) was added to the mixture. After being stirred for 30 minutes, the solvent was removed in vacuo. The residue was partitioned between ethyl acetate and lN-NaOH and the organic layer was washed with brine. The dried solvent was evaporated in vacuo. The residue was purified by chromatography on silica gel to give and the obtained residue was purified by chromatography on silica gel to give (S)-3-{[2-(4,5-diphenyloxazol-2-yl)-2-cyclohexen-1-yl]methyl}- benzamide (0.03 g).

IR (Nujol): 1660 cm$^{-1}$; NMR (CDCl$_3$, δ): 1.4–1.0 (4H, m), 2.2–2.4 (2H, m), 2.65 (1H, dd, J=9.8, 13.0 Hz), 3.15 (1H, m), 3.20 (1H, dd, J=4.0, 13.0 Hz), 5.5 (1H, br s), 6.1 (1H, br s), 6.92 (1H, m), 7.2–7.9 (13H, m); Mass (m/z): 435 (M+H)$^+$.

EXAMPLE 14

The following compounds were obtained according to a similar manner to that of Example 13.
(1) 3-{[(1S,2S)-2-(4,5-Diphenyloxazol-2-yl)-1-cyclopentyl]-methyl}benzamide IR (Nujol): 1650 cm$^{-1}$; NMR (CDCl$_3$, δ): 1.5–2.4 (6H, m), 2.4–2.8 (3H, m), 3.48 (1H, m), 5.6 (1H, br s), 6.09 (1H, br s), 7.2–7.7 (14H, m); Mass (m/z): 423 (M+H)$^+$.

(2) 3-{[(1S,2R)-2-(4,5-Diphenyloxazol-2-yl)-1-cyclopentyl]-methyl}benzamide

IR (Nujol): 1650 cm$^{-1}$; NMR (CDCl$_3$, δ); 1.4–2.5 (6H, m), 2.6–3.0 (4H, m), 5.4 (1H, br s), 6.0 (1H, br s), 7.2–7.7 (14H, m); Mass (m/z): 423 (M+H)$^+$.

(3) 3-{[2-(4,5-Diphenyloxazol-2-yl)-1-cyclopenten-1-yl]-methyl}benzamide

IR (Nujol): 1660 cm$^{-1}$; NMR (CDCl$_3$, δ): 1.8–2.0 (2H, m), 2.4–2.6 (2H, m), 2.9- 3.1 (2H, m), 4.19 (2H, s), 4.67 (1H, br s), 5.96 (1H, br s), 7.2–7.8 (14H, m); Mass (m/z): 421 (M+H)$^+$.

EXAMPLE 15

To a solution of (S)-3-{(2-(4,5-diphenyloxazol-2-yl)-2-cyclohexen-1-yl1methyl}benzoic acid (3 g) in a methanol (30 ml) was added lN-NaOH solution (6.9 ml). After being stirred for 5 minutes, the solvent was removed in vacuo to give sodium (S)-3-{[2-(4,5-diphenyloxazol-2-yl)-2-cyclohexen-1-yl]methyl}benzoate (3 g). NMR (DMSO-d$_6$): 1.4–2.0 (4H, m), 2.2–2.4 (2H, m), 3.0–3.1 (1H, m), 6.91 (1H, m), 7.0–7.8 (12H, m), 7.83 (1H, s);

EXAMPLE 16

To a solution of (S)-3-{[2-(4,5-diphenyloxazol-2-yl)-2-cyclohexen-1-yl]methyl}benzoic acid (0.2 g) in a tetrahydrofuran (10 ml) were added isobutyl chloroformate (0.15 ml.) and triethylamine (0.2 ml) at 0° C. under N$_2$. After being stirred for 30 minutes, NH$_3$ (5 ml, 4M solution in methanol) was added to the mixture. After being stirred for 30 minutes, the solvent was removed in vacuo. The residue was partitioned between ethyl acetate and 1N-NaOH and the organic layer was washed with brine. The dried solvent was evaporated in vacuo. The residue and 10% Pd/C (0.2 g) in methanol (20 ml) was stirred under H$_2$ for 8 hours. The catalyst was filtered off and filtrate was evaporated in vacuo. The residue was purified by chromatography on silica gel to give and the obtained residue was purified by chromatography on silica gel to give 3-{[(1S)-2-(4,5-diphenyloxazol-2-yl)-1-cyclohexyl]methyl}benzamide (0.11 g).

IR (neat): 3300, 3200, 1660 cm$^{-1}$; NMR (CDCl$_3$,δ): 1.2–2.4 (9H, m), 2.5–2.8 (2H, m), 3.2 (1H, m), 5.5 (1H, br s), 6.0 (1H, br s), 7.2–7.8 (14H, m); Mass (m/z): 437 (M+H)$^+$.

EXAMPLE 17

A dimethylformamide (8 ml) - MeOH (4 ml) solution of 3-{[2-(4,5-diphenyloxazol-2-yl)-2-cyclopenten-1-yl]

methyl}-phenyl trifluoromethanesulfonate (2.24 g), Palladium(II) acetate (64 mg), 1,3-bis(diphenylphosphino) propane (106 mg) and triethylamine (1.2 ml) was saturated with CO gas. The solution was stirred for 14 hours at 70° C. under CO atmosphere. The solvent was evaporated in vacuo and the residue was partitioned between ethyl acetate and water. The organic layer was washed with 1N hydrochloric acid, water and brine. After dried over $MgSO_4$, the organic solvent was evaporated in vacuo. The residue was purified by silica gel chromatography to afford methyl 3-{[2-(4,5-diphenyloxazol-2-yl)-2-cyclopenten-1-yl]methyl}benzoate (1.17 g).

IR (neat): 1710, 1630 $cm^{-1}$; NMR ($CDCl_3$, δ): 1.65–1.97 (1H, m), 1.97–2.19 (1H, m), 2.39–2.50 (2H, m), 2.71 (1H, dd, J=13.4, 9.2 Hz), 3.46 (1H, dd, J=13.4, 4.1 Hz), 3.78 (1H, m), 3.88 (3H, s), 6.70 (1H, m), 7.29–7.46 (8H, m), 7.59–7.72 (4H, m), 7.83–7.93 (2H, m).

EXAMPLE 18

To a methanol solution (7 ml) of methyl 3-{[2-(4,5-diphenyloxazol-2-yl)-2-cyclopenten-1-yl]methyl}benzoate (1.15 g) was added 1N aqueous sodium hydroxide solution (4 ml). The solution was stirred overnight at room temperature. The solvent was evaporated in vacuo and the residue was partitioned between ethyl acetate and 1N hydrochloric acid. The organic layer was washed with brine. After dried over $MgSO_4$, the organic solvent was evaporated in vacuo to afford 3-{[2-(4,5-diphenyloxazol-2-yl)-2-cyclopenten-1-yl]methyl}-benzoic acid (1.02 g).

IR (Nujol) 1680 $cm^{-1}$; NMR ($CDCl_3$, δ): 1.72–1.92 (1H, m), 2.00–2.20 (1H, m), 2.38–2.52 (2H, m), 2.74 (1H, dd, J=12.7, 9.1 Hz), 3.46 (1H, dd, J=12.7, 4.2 Hz), 3.60 (1H, m), 6.72 (1H, m), 7.26–7.72 (12H, m), 7.90–8.01 (2H, m); Mass (m/z): 422 $(M+H)^+$.

EXAMPLE 19

To a tetrahydrofuran solution (10 ml) of 3-{[2-(4,5-diphenyloxazol-2-yl)-2-cyclopenten-1-yl]methyl}benzoic acid (0.30 g) and triethylamine (0.15 ml) was added ethyl chloroformate (0.15 ml) at 0° C. The solution was stirred for 30 minutes at the same temperature. Then aqueous ammonia (10 ml) was added to the solution. After stirred for 6 hours at 0° C., the solution was partitioned between ethyl acetate and water. The organic layer was washed with water, 1N hydrochloric acid, water and brine. After dried over $MgSO_4$, the solvent was evaporated in vacuo to afford 3-{[2-(4,5-diphenyloxazol-2-yl)-2-cyclopenten-1-yl]methyl}benzamide (0.24 g).

IR (Nujol): 3800, 3160, 1640, 1620 $cm^{-1}$; NMR ($CDCl_3$, δ): 1.72–2.20 (2H, m), 2.38–2.54 (2H, m), 2.72 (1H, dd, J=13.5, 9.1 Hz), 3.43 (1H, dd, J=13,5, 4.0 Hz), 3.60 (1H, m), 6.71 (1H, m), 7.34–7.52 (9H, m), 7.57–7.70 (7H, m); Mass (m/z): 421 $(M+H)^+$, 403 $(M-NH_3)^+$.

EXAMPLE 20

3-{[2-(4,5-Diphenyloxazol-2-yl)-2-cyclopenten-1-yl]methyl}benzamide (75 mg) was hydrogenated over 5% Pd/C (3 mg) in methanol (20 ml) at room temperature at 3 atm for 7 hours. The mixture was filtered and the filtrate was evaporated in vacuo. The residue was triturated with a mixture of ether and n-hexane to afford 3-{[2-(4,5-diphenyloxazol-2-yl)-1-cyclopentyl]methyl}benzamide (54 mg).

IR (KBr): 3334, 3199, 3059, 2954, 2869, 1662 $cm^{-1}$; NMR (DMSO-$d_6$, δ): 1.20–3.12 (9H, m), 3.48 (1H, m), 7.15–8.00 (16H, m); Mass (m/z): 423 $(M+H)^+$, 405 $(M-NH_3)^+$.

EXAMPLE 21

To a solution of ethyl (S)-{3-{[2-(4,5-diphenyloxazol-2-yl)-2-cyclohexen-1-yl]methyl}phenoxy}acetate (0.5 g) in tetrahydrofuran (5 ml) was added $NH_3$ (5 ml, 4N methanol solution). After being stirred for 24 hours, the solvent was removed. The residue was purified by chromatography on silica gel to give (S)-{3-{[2-(4,5-diphenyloxazol-2-yl)-2-cyclohexen-1-yl]methyl}phenoxy}acetamide (220 mg).

IR (Nujol): 1640 $cm^{-1}$; NMR ($CDCl_3$, δ): 1.4–2.0 (4H, m), 2.2–2.4 (2H, m), 2.56 (1H, dd, J=9.8, 12.8 Hz), 3.20 (1H, m), 3.32 (1H, dd, J=4.0, 12.8 Hz), 4.46 (2H, s), 5.8 (1H, br s), 6.5 (1H, br s), 6.8–7.8 (14H, m); Mass (m/z): 465 $(M+H)^+$.

EXAMPLE 22

To a solution of 2-(4,5-diphenyloxazol-2-yl)-3-(3-methoxybenzyl)bicyclo[2.2.1]hept-2-ene (3.4 g) in dichloromethane (35 ml) was added $BBr_3$ (17 ml, 1M solution in dichloromethane) at 0° C. After being stirred for 2 hours, the solvent was evaporated in vacuo. The residue was diluted with ethyl acetate, and the mixture was washed with water and brine. The dried solvent was evaporated in vacuo and dissolved in dichloromethane (20 ml). To the solution were added trifluoromethanesulfonic anhydride (0.8 ml) and 2,6-lutidine (1.1 ml) −78° C. After being stirred for 2 hours, the solvent was evaporated in vacuo. The residue was diluted with ethyl acetate, and the mixture was washed with water, sat. $NaHCO_3$ and brine. The dried solvent was evaporated in vacuo and the residue was purified by chromatography on silica gel to give a Tf-compound [3-{[3-(4,5-diphenyloxazol-2-yl)bicyclo[2.2.1]hept-2-en-2-yl]methyl}phenyl trifluoromethansulfonate] (1.6 g).

To a solution of the Tf-compound (1.6 g) in a mixture of methanol (10 ml) and DMF (20 ml) were added 1,3-bis(diphenylphosphino)propane (480 mg), palladium acetate (260 mg), and triethylamine (1.2 ml). After being stirred for 5 hours at 80° C. under carbone monooxide atmosphere, the mixture was partitioned between ethyl acetate and water and the organic layer was washed with 1N-HCl, sat. $NaHCO_3$, and brine. The dried solvent was evaporated in vacuo and the obtained solid was washed with ether to afford methyl 3-{[3-(4,5-diphenyloxazol-2-yl)bicyclo [2.2.1]hept-2-en-2-yl]-methyl}benzoate (1.0 g).

IR (Nujol): 1720 $cm^{-1}$; NMR ($CDCl_3$, δ): 1.0–2.0 (6H, m), 2.85 (1H, br s), 3.62 (1H, br s), 3.86 (1H, d, J=14 Hz), 3.89 (3H, s), 4.40 (1H, d, J=14 Hz), 7.2–8.0 (14H, m); Mass (m/z): 462 $(M+H)^+$.

EXAMPLE 23

The following compound was obtained according to a similar manner to that of Example 22.

Methyl 3-{[2-(4,5-diphenyloxazol-2-yl)-2-cyclohepten-1-yl]methyl}benzoate

IR (Nujol): 1720 $cm^{-1}$; NMR ($CDCl_3$, δ): 1.4–2.0 (6H, m), 2.4–2.6 (2H, m), 2.91 (1H, dd, J=10.0, 14.0 Hz), 3.09 (1H, dd, J=6.6, 14 Hz), 3.81 (3H, s), 7.08 (1H, t, J=8.0 Hz), 7.2–7.8 (12H, m), 7.80 (1H, d, J=8 Hz), 8.00 (1H, s); Mass (m/z): 464 $(M+H)^+$.

EXAMPLE 24

To a solution of methyl 3-{[3-(4,5-diphenyloxazol-2-yl) bicyclo[2.2.1]hept-2-en-2-yl]methyl}benzoate (1.0 g) in a mixture of methanol (10 ml) and THF (10 ml) was added 1N-NaOH solution (11 ml). After being stirred for 5 minutes, the solvent was removed in vacuo. The residue was dissolved in a mixture of ethyl acetate and 1N-HCl solution. The organic layer was washed with brine and dried over $MgSO_4$. The solution was evaporated in vacuo to give 3-{[3-(4,5-diphenyloxazol-2-yl)bicyclo[2.2.1]hept-2-en-2-yl]methyl}-benzoic acid (1.0 g).

IR (Nujol): 1690 $cm^{-1}$; NMR ($CDCl_3$, δ): 1.0–2.0 (6H, m), 2.86 (1H, br s), 3.68 (1H, br s), 3.86 (1H, d, J=15 Hz), 4.39 (1H, d, J=14 Hz), 7.2–8.2 (14H, m); Mass (m/z): 448 $(M+H)^+$.

EXAMPLE 25

The following compounds described in (1) to (3) were obtained in a similar manner to that of Example 24.
(1) 3-{[2-(4,5-Diphenyloxazol-2-yl)-2-cyclohepten-1-yl]-methyl}benzoic acid IR (Nujol): 1690 $cm^{-1}$; NMR ($CDCl_3$, δ): 1.4–2.0 (6H, m), 2.4–2.6 (2H, m), 2.94 (1H, dd, J=10.0, 14.0 Hz), 3.12 (1H, dd, J=10, 14Hz), 4.11 (1H, m), 7.11 (1H, t, J=8.0 Hz), 7.2–7.8 (12H, m), 7.89 (1H, d, J=8 Hz), 8.10 (1H, s); Mass (m/z): 450 $(M+H)^+$.
(2) (S)-3-{[2-(4,5-Diphenyloxazol-2-yl)-2-cyclohexen-1-yl]-methyl}phenylacetic acid; NMR ($CDCl_3$, δ): 1.4–1.8 (4H, m), 2.1–2.4 (2H, m), 2.5–2.8 (1H, m), 3.1–3.4 (2H, m), 6.93 (1H, m), 7.0–8.2 (14H, m); Mass (m/z): 450 $(M+H)^+$.
(3) 3-}3-{[2-(4,5-diphenyloxazol-2-yl)-2-cyclohexen-1-yl]-methyl}phenyl)propionic acid sodium salt IR (Nujol): 1580 $cm^{-1}$; NMR (DMSO-$d_6$, δ): 1.4–2.0 (4H, m), 2.1–2.5 (5H, m), 2.6–2.9 (2H, m), 2.9–3.2 (2H, m), 6.8–7.2 (4H, m), 7.2–7.8 (10H, m); Mass (m/z): 464 (M+H-Na)$^+$.

EXAMPLE 26

To a solution of 3-{[3-(4,5-diphenyloxazol-2-yl)-bicyclo [2.2.1]hept-2-en-2-yl]methyl}benzoic acid (0.46 g) in a THF (10 ml) were added isobutyl chloroformate (0.26 ml) and triethylamine (0.3 ml) at 0° C. under $N_2$. After being stirred for 30 minutes, $NH_3$ (5 ml, 4M solution in methanol) was added to the mixture. After being stirred for 30 minutes, the solvent was removed in vacuo. The residue was partitioned between ethyl acetate and 1N-NaOH and the organic layer was washed with brine. The dried solvent was evaporated in vacuo to give 3-{[3-(4,5-diphenyloxazol-2-yl) bicyclo[2.2.1]hept-$^2$-en-2-yl]methyl}benzamide (0.2 g).

IR (neat): 3350, 3150, 1660 $cm^{-1}$;

NMR ($CDCl_3$, δ): 1.2–2.4 (6H, m), 2.86 (1H, br s), 3.61 (1H, br s), 3.82 (1H, d, J=14 Hz), 4.40 (1H, d, J=14 Hz), 7.2–7.8 (14H, m); Mass (m/z): 447 $(M+H)^+$.

EXAMPLE 27

The following compound was obtained in a similar manner to that of Example 26.
3-{[2-(4,5-Diphenyloxazol-2-yl)-2-cyclohepten-1-yl] methy 1}-benzamide IR (neat): 3350, 3150, 1660 $cm^{-1}$; NMR ($CDCl_3$, δ): 1.4–2.0 (6H, m), 2.42 (2H, m), 2.91 (1H, dd, J=8.6, 13.4 Hz), 3.10 (1H, dd, J=7.2, 13.4 Hz), 3.78 (1H, m), 7.09 (1H, t, J=8 Hz), 7.2–7.8 (14H, m); Mass (m/z): 449 $(M+H)^+$.

EXAMPLE 28

A solution of (S)-3-{[2-(4,5-diphenyloxazol-2-yl)-2-cyclohexen-1-yl]methyl}benzoic acid (0.5 g), diphenylphosphoryl azide (0.30 ml), and triethylamine (0.2 ml) in toluene (20 ml) was stirred for 1 hour under reflux. To the mixture was added benzylalcohol and stirred for 15 hours under reflux. The cooled solvent was evaporated in vacuo and the obtained residue was purified by chromatography on silica gel to afford benzyl (S)-3-{[2-(4,5-diphenyloxazol-2-yl)-2-cyclohexen-1-yl]methyl}phenylcarbamate (0.4 g).

IR (Nujol): 1720 $cm^{-1}$; NMR ($CDCl_3$, δ): 1.4–1.8 (4H, m), 2.3 (1H, m), 2.53 (1H, dd, J=9.6, 12 Hz), 3.20 (1H, m), 3.28 (1H, dd, J=4.0, 12 Hz), 5.19 (2H, s), 6.60 (1H, s), 6.86 (1H, m), 7.03 (1H, d, J=8 Hz), 7.2–7.8 (13H, m); Mass (m/z): 541 $(M+H)^+$.

EXAMPLE 29

A mixture of 3-{[3-(4,5-diphenyloxazol-2-yl)bicyclo-[2.2.1]hept-2-en-2-yl]methyl}benzoic acid (0.3 g) and 10% Pd/C (0.1 g) in methanol (20 ml) was stirred under $H_2$ for 8 hours. The catalyst was filtered off and filtrate was evaporated in vacuo to give 3-{[3-(4,5-diphenyloxazol-2-yl)-bicyclo[2.2.1]hept-2-yl]methyl}benzoic acid (0.27 g).

IR (Nujol): 1690 $cm^{-1}$; NMR ($CDCl_3$, δ): 1.2–2.8 (11H, m), 3.60 (1H, m), 7.2–8.0 (14H, m); Mass (m/z) 450 $(M+H)^+$.

EXAMPLE 30

The following compounds described in (1) to (4) were obtained in a similar manner to that of Example 29.
(1) 3-{[3-(4,5-Diphenyloxazol-2-yl)bicyclo[2.2.1]hept-2-yl]methyl}benzamide IR (Nujol): 1660 $cm^{-1}$; NMR ($CDCl_3$, δ): 1.2–2.8 (11H, m), 3.52 (1H, m), 7.2–7.8 (14H, m); Mass (m/z): 449 $(M+H)^+$.
(2) 3-{[2-(4,5-Diphenyloxazol-2-yl)-1-cycloheptyl] methyl}-benzoic acid IR (Nujol): 1690 $cm^{-1}$; NMR ($CDCl_3$, δ): 1.2–2.2 (10H, m), 2.5–3.0 (3H, m), 3.34 (1H, m), 7.2–6.0 (12H, m), 7.8–8.0 (2H, m); Mass (m/z): 452 $(M+H)^+$.
(3) 3-{[2-(4,5-Diphenyloxazol-1-yl)-1-cycloheptyl] methyl}-benzamide IR (Nujol): 1640 $cm^{-1}$; NMR ($CDCl_3$, δ) 1.3–2.2 (10H, m), 2.4–3.0 (3H, m), 3.28 (1H, m), 7.2–7.8 (10H, m); Mass (m/z): 451 $(M+H)^+$.
(4) (S)-3-{[2-(4,5-Diphenyloxazol-2-yl)-1-cyclohexyl]-methyl}aniline IR (Nujol): 1600 $cm^{-1}$; NMR ($CDCl_3$, δ): 1.4–2.8 (11H, m), 3.22 (1H, m), 6.4–6.6 (2H, m), 7.0–7.8 (12H, m); Mass (m/z): 409 $(M+H)^+$.

EXAMPLE 31

To a solution of (S)-3-{[2-(4,5-diphenyloxazol-2-yl)-1-cyclohexyl]methyl}aniline (70 mg) in dichloromethane (10 ml) were added pyridine (1 ml) and MsCl (0.032 ml). After stirred for 2 hours at the room temperature, the mixture was partitioned between ethyl acetate and water and the organic layer was washed with 1N-HCl, sat. NaHCO3, and brine. The dried solvent was evaporated in vacuo and the obtained solid was washed with ether to afford (S)-N-{3-{[2-(4,5-diphenyloxazol-2-yl)-1-cyclohexyl]methyl}phenyl}-methanesulfonamide (0.05 g).

IR (Nujol): 1600 $cm^{-1}$; NMR ($CDCl_3$, δ): 1.2–2.8 (11H, m), 2.87 (3H, s), 3.2 (1H, m), 6.37 (1H, m), 6.9–7.8 (14H, m); Mass (m/z): 487 $(M+H)^+$.

EXAMPLE 32

To a solution 4,5-diphenyloxazole (1.2 g) in THF (20 ml) was added n-BuLi (3.7 ml, 1.6M solution in hexane) at −78° C. After stirred for 30 minutes at the same temperature, a solution of 2-(3-cyanobenzyl)hexanone (1.0 g) in THF (10 ml) was added to the mixture. After stirred for 2 hours at the same temperature, the mixture was partitioned between ethyl acetate and water. The organic layer was washed with 1N-HCl, water, sat. NaHCO$_3$ and brine. The dried solvent was evaporated in vacuo and the residue was purified by chromatography on silica gel to give alcohol compound. A mixture of the alcohol compound and p-toluenesulfonic acid (0.01 g) in toluene (30 ml) was stirred for 7 hours under reflux. The solution was washed with water, sat. NaHCO$_3$, and brine, dried over MgSO$_4$, and evaporated in vacuo. The residue was purified by chromatography on silica gel to afford 3-{[2-(4,5-diphenyloxazol-2-yl)-2-cyclohexen-1-yl]-methyl}benzonitrile (0.86 g).

IR (Nujol): 2200 cm$^{-1}$; NMR (CDCl$_3$, δ): 1.4–1.9 (4H, m), 2.2–2.4 (2H, m), 2.59 (1H, dd, J=10.0, 13.2 Hz), 3.1–3.3 (1H, m), 3.33 (1H, dd, J=3.4, 13.2 Hz), 6.92 (1H, d, J=3.8 Hz), 7.2–7.8 (14H, m); Mass (m/z): 417 (M+H)$^+$.

EXAMPLE 33

The following compound was obtained in a similar manner to that of Example 32.

Ethyl 3-{3-{[2-(4,5-diphenyloxazol-2-yl)-2-cyclohexen-1-yl]methyl}phenyl}propionate IR (Nujol): 1730 cm$^{-1}$; NMR (CDCl$_3$, δ): 1.22 (3H, t, J=8 Hz), 1.4–2.0 (4H, m), 2.2–2.4 (2H, m), 2.5–2.8 (3H, m), 2.8–3.0 (2H, m), 3.1–3.3 (2H, m), 4.17 (2H, q, J=8 Hz), 6.8–7.1 (2H, m), 7.1–7.8 (13H, m); Mass (m/z): 492 (M+H)$^+$.

EXAMPLE 34

To a solution of (S)-3-{[2-(4,5-diphenyloxazol-2-yl)-2-cyclohexen-1-yl]methyl}phenyl trifluoromethanesulfonate (1.17 g) in dichloromethane (100 ml) were added 5-(2-boronophenyl)-2-(triphenylmethyl)-2H-tetrazole (1.16 g), tetrakis(triphenylphosphine)palladium (600 mg), and K$_2$CO$_3$ (630 mg) in a mixture of DMF and water. After being stirred for 8 hours at 100° C., the solvent was evaporated in vacuo. The residue was purified by chromatography on silica gel to give (S)-2-(4,5-diphenyloxazol-2-yl)-1-{3-{2-[2-(triphenyl-methyl)tetrazol-5-yl]phenyl}benzyl}-2-cyclohexene (0.83 g).

IR (Nujol): 1600 cm$^{-1}$; NMR (CDCl$_{3, δ)}$: 1.4–1.8 (4H, m), 2.2–2.4 (3H, m), 3.0–3.2 (2H, m), 6.8–7.0 (6H, m), 7.0–8.0 (27H, m);

EXAMPLE 35

To a solution of (S)-2-(4,5-diphenyloxazol-2-yl)-1-{3-{2-[2-(triphenylmethyl)tetrazol-5-yl]phenyl}benzyl}-2-cyclohexene (0.8 g) in methanol (20 ml) was added conc. HCl solution (2 ml). After being stirred for 4 hours, the solvent was evaporated in vacuo. The residue was purified by chromatography on silica gel to give (S)-2-(4,5-diphenyloxazol-2-yl)-1-{3-[2-(tetrazol-5-yl)phenyl]benzyl}-2-cyclohexene (50 mg).

IR (Nujol): 1600 cm$^{-1}$; NMR (CDCl$_3$, δ): 1.2–1.8 (4H, m), 2.2–2.4 (2H, m), 2.6–3.2 (3H, m), 6.8–7.6 (19H, m), 8.03 (1H, d, J=8 Hz); Mass (m/z): 536 (M+H)$^+$.

EXAMPLE 36

To a solution of 2-(4,5-diphenyloxazol-2-yl)-1-(3-cyanobenzyl)-2-cyclohexene (400 mg) in DMF (8 ml) were added NaN$_3$ (100 mg) and NH$_4$Cl (80 mg). After stirred for 12 hours at 120° C., the mixture was partitioned between ethyl acetate and water and the organic layer was washed with 1N-HCl and brine. The dried solvent was evaporated in vacuo and the obtained solid was washed with a mixture of ether and n-hexane to afford 2-(4,5-diphenyloxazol-2-yl)-1-{3-(1H-tetrazol-5-yl)benzyl}-2-cyclohexene (0.36 g).

NMR (CDCl$_3$, δ): 1.3–2.0 (4H, m), 2.2–2.5 (2H, m), 2.66 (1H, dd, J=10, 14 Hz), 3.1–3.3 (2H, m), 6.91 (1H, t, J=4.2 Hz), 7.1–7.8 (12H, m), 7.8–8.0 (2H, m); Mass (m/z): 460 (M+H)$^+$.

EXAMPLE 37

To a solution of (S)-3-{[2-(4,5-diphenyloxazol-2-yl)-2-cyclohexen-1-yl]methyl}benzoic acid (0.2 g) in CH$_2$Cl$_2$ (10 ml) was added SOCl$_2$ (1 ml) and stirred for 1 hour at the room temperature. After the solvent was evaporated in vacuo, the residue was dissolved in a mixture of THF and CH$_3$CN. To the solution were added (trimethylsilyl)diazomethane (0.34 ml) and triethylamine (0.1 ml) at 0° C. After stirred for 48 hours at the same temperature, the solvent was evaporated in vacuo, and benzylalcohol (1.8 ml) and 2,4,6-collidine (1.8 ml) were added to there. After stirred for 20 minutes at 180° C., the mixture was diluted with toluene and purified by chromatography on silica gel to afford benzyl (S)-3-{[2-(4,5-diphenyloxazol-2-yl)-2-cyclohexen-1-yl]methyl}phenylacetate (0.14 g).

IR (Nujol): 1720 cm$^{-1}$; NMR (CDCl$_3$, δ): 1.4–1.8 (4H, m), 2.3–2.5 (2H, m), 2.4–2.6 (1H, m), 3.0–3.4 (2H, m), 6.92 (1H, m), 7.0–8.0 (19H, m); Mass (m/z): 540 (M+H)$^+$.

EXAMPLE 38

To a solution of 4,5-diphenyloxazole (990 mg) in THF (15 ml) was added n-BuLi (1.56M solution in hexane, 2.87 ml) at −60° C. and stirred for 1 hour. To the mixture was added a solution of 2-(3-methoxy-2-methylbenzyl)cyclohexanone (945 mg) in THF (4 ml), warmed to 5° C., and stirred for 2 hours. To the reaction mixture was added 1N HCl and extracted with EtOAc. The organic layer was washed with water, saturated sodium hydrogen carbonate, water, and brine, dried over magnesium sulfate, evaporated in vacuo. The residue was dissolved in toluene (45 ml) and p-TsOH.H$_2$O (79 mg) was added. The mixture was refluxed for 48 hours, cooled to room temperature, diluted with EtOAc, washed with saturated sodium hydrogen carbonate, water, and brine, dried over magnesium sulfate, evaporated in vacuo. The residue was purified by silica gel column chromatography (hexane-EtOAc 15:1 to 10:1) to give 2-[1-(3-methoxy-2-methylbenzyl)-2-cyclohexen-2-yl]-4,5-diphenyloxazole (1.19 g) as an amorphous solid.

IR (KBr): 3057, 2933, 2862, 1643, 1583, 1537, 1462, 1444, 1255 cm$^{-1}$; NMR (CDCl$_3$, δ): 1.38–2.40 (6H, m), 2.42 (3H, s), 2.62 (1H, dd, J=13.1, 10.8 Hz), 3.10–3.28 (1H, m), 3.35 (1H, dd, J=13.1, 3.8 Hz), 3.80 (3H, s), 6.70 (1H, d, J=7.9 Hz), 6.82–6.95 (2H, m), 7.07 (1H, dd, J=7.9, 7.9 Hz), 7.30–7.50 (6H, m), 7.58–7.77 (4H, m); Mass (m/z): 436 (M+H)$^+$.

EXAMPLE 39

The following compounds described in (1) to (4) were obtained in a similar manner to that of Example 38.
(1) 2-[1-(3-Methoxy-4-methylbenzyl)-2-cyclohexen-2-yl]-4,5-diphenyloxazole IR (neat): 3053, 2933, 2860, 1610, 1585, 1533, 1506, 1446, 1411, 1255 cm$^{-1}$; NMR (CDCl$_3$, δ): 1.40–1.90 (4H, m), 2.17 (3H, s), 2.18–2.40 (2H, m), 2.52 (1H, dd, J=12.8, 9.9 Hz), 3.06–3.30 (2H, m), 3.79 (3H, s), 6.79 (1H, d, J=7.3

Hz), 6.84–6.95 (2H, m), 7.03 (1H, d, J=7.3 Hz), 7.23–7.42 (6H, m), 7.55–7.75 (4H, m); Mass (m/z): 436 (M+H)+.

(2) 2-[1-(3-Methoxy-5-methylbenzyl)-2-cyclohexen-2-yl]-4,5-diphenyloxazole

IR (neat): 3053, 2933, 2860, 1595, 1533, 1462, 1446, 1294, 1151 cm−1; NMR (CDCl3, δ): 1.38–1.95 (4H, m), 2.10–2.58 (3H, m), 2.30 (3H, s), 3.08–3.27 (2H, m), 3.76 (3H, s), 6.55 (1H, s), 6.72 (1H, s), 6.77 (1H, s), 6.92 (1H, dd, J=4.0, 4.0 Hz), 7.23–7.45 (6H, m), 7.58–7.78 (4H, m); Mass (m/z): 436 (M+H)+.

(3) 2-[1-(5-Methoxy-2-methylbenzyl)-2-cyclohexen-2-yl]-4,5-diphenyloxazole

IR (neat): 3055, 2935, 2862, 1606, 1535, 1502, 1446, 1250 cm−1; NMR (CDCl3, δ): 1.38–1.95 (4H, m), 2.07–2.47 (2H, m), 2.41 (3H, s), 2.60 (1H, dd, J=14.5, 12.0 Hz), 3.10–3.33 (2H, m), 3.75 (3H, s), 6.65 (1H, dd, J=8.4, 2.7 Hz), 6.82–6.96 (2H, m), 7.04 (1H, d, J=8.4 Hz), 7.20–7.43 (6H, m), 7.53–7.76 (4H, m); Mass (m/z): 436 (M+H)+.

(4) 2-[1-(2-Methoxybenzyl)-2-cyclohexen-2-yl]-4,5-diphenyloxazole

IR (neat): 3057, 2935, 2862, 1601, 1535, 1493, 1444, 1242 cm−1; NMR (CDCl3, δ): 1.40–2.00 (4H, m), 2.10–2.38 (2H, m), 2.80 (1H, dd, J=12.9, 10.3 Hz), 3.05–3.33 (2H, m), 3.78 (3H, s), 6.75–6.95 (3H, m), 7.07–7.43 (8H, m), 7.55–7.77 (4H, m); Mass (m/z): 422 (M+H)+.

EXAMPLE 40

To a solution of 2-[1-(3-methoxy-2-methylbenzyl)-2-cyclohexen-2-yl]-4,5-diphenyloxazole (1.16 g) in CH2Cl2 (25 ml) was added boron tribromide (1M solution in CH2Cl2, 5.32 ml) at −60° C. and the mixture was warmed to 5° C. After stirring for 1 hour at the same temperature, the reaction mixture was stirred for further 1 hour at room temperature. To the mixture was added water under ice-cooling, extracted with EtOAc. The organic layer was washed with water, saturated sodium hydrogen carbonate, water, and brine, dried over magnesium sulfate, evaporated in vacuo. The residue was purified by silica gel column chromatography (hexane-EtOAc 5:1) to give 3-{[2-(4,5-diphenyloxazol-2-yl)-2-cyclohexen-1-yl]methyl}-2-methylphenol (903.8 mg) as an amorphous solid.

IR (KBr): 3330, 3059, 2933, 2862, 1645, 1585, 1537, 1466, 1446, 1273 cm−1; NMR (CDCl3, δ): 1.35–2.40 (6H, m), 2.45 (3H, s), 2.60 (1H, dd, J=13.3, 11.1 Hz), 3.07–3.25 (1H, m), 3.37 (1H, dd, J=13.3, 3.8 Hz), 4.67 (1H, s), 6.62 (1H, d, J=7.9 Hz), 6.80 (1H, d, J=7.9 Hz), 6.85–7.02 (2H, m), 7.20–7.45 (6H, m), 7.55–7.75 (4H, m); Mass (m/z): 422 (M+H)+.

EXAMPLE 41

The following compounds described in (1) to (4) were obtained in a similar manner to that of Example 40.

(1) 5-{[2-(4,5-Diphenyloxazol-2-yl)-2-cyclohexen-1-yl]methyl}-2-methylphenol

IR (KBr): 3319, 3062, 2931, 2858, 1589, 1523, 1446, 1419, 1242, 1119 cm−1; NMR (CDCl3, δ): 1.40–1.90 (4H, m), 2.08–2.36 (2H, m), 2.20 (3H, s), 2.47 (1H, dd, J=12.7, 9.9 Hz), 3.05–3.27 (2H, m), 4.73 (1H, s), 6.70–6.83 (2H, m), 6.83–6.95 (1H, m), 7.02 (1H, d, J=7.4 Hz), 7.22–7.45 (6H, m), 7.55–7.75 (4H, m); Mass (m/z): 422 (M+H)+.

(2) 3-{[2-(4,5-Diphenyloxazol-2-yl)-2-cyclohexen-1-yl]methyl}-5-methylphenol

IR (KBr): 3330, 3032, 2931, 2858, 1595, 1535, 1444, 1311, 1298, 1153 cm−1; NMR (CDCl3, δ): 1.40–1.90 (4H, m), 2.07–2.56 (3H, m), 2.27 (3H, s), 3.06–3.26 (2H, m), 4.82 (1H, s), 6.47 (1H, s), 6.61 (1H, s), 6.74 (1H, s), 6.92 (1H, dd, J=4.0, 4.0 Hz), 7.22–7.45 (6H, m), 7.55–7.77 (4H, m); Mass (m/z): 422 (M+H)+.

(3) 3-{[2-(4,5-Diphenyloxazol-2-yl)-2-cyclohexen-1-yl]methyl}-4-methylphenol

IR (KBr): 3356, 2935, 2862, 1606, 1587, 1535, 1502, 1444 cm−1; NMR (CDCl3, δ): 1.38–1.98 (4H, m), 2.10–2.47 (2H, m), 2.40 (3H, s), 2.56 (1H, dd, J=14.3, 11.8Hz), 3.10–3.33 (2H, m), 4.75 (1H, s), 6.57 (1H, dd, J=8.3, 2.7 Hz), 6.76 (1H, d, J=2.7 Hz), 6.91 (1H, dd, J=3.9, 3.9Hz), 6.98 (1H, d, J=8.3Hz), 7.20–7.43 (6H, m), 7.53–7.73 (4H, m); Mass (m/z): 422 (M+H)+.

(4) 2-{[2-(4,5-Diphenyloxazol-2-yl)-2-cyclohexen-1-yl]methyl}phenol

IR (KBr): 3180, 3057, 2937, 1645, 1579, 1535, 1485, 1446, 1344, 1227 cm−1; NMR (CDCl3, δ): 1.30–2.00 (4H, m), 2.15–2.55 (3H, m), 2.82–2.98 (1H, m), 3.28–3.43 (1H, m), 6.72–7.50 (11H, m), 7.54–7.77 (4H, m); Mass (m/z): 408 (M+H)+.

EXAMPLE 42

To a solution of 3-{[2-(4,5-diphenyloxazol-2-yl)-2-cyclohexen-1-yl]methyl}-2-methylphenol (894 mg) and 2,6-lutidine (0.494 ml) in CH2Cl2 (18 ml) was added trifluoromethanesulfonic anhydride (0.534 ml) at 5° C. and the mixture was stirred for 1 hour. The solvent was removed in vacuo and the residue was diluted with EtOAc, washed with water, 1N HCl, water, and brine, dried over magnesium sulfate, evaporated in vacuo. The residue was purified by silica gel column chromatography (hexane-EtOAc 15:1) to give 3-{[2-(4,5-diphenyloxazol-2-yl)-2-cyclohexen-1-yl]methyl}-2-methylphenyl trifluoromethanesulfonate (960.8 mg) as an oil.

IR (neat): 3059, 2939, 1537, 1448, 1419, 1250, 1217, 1140 cm−1; NMR (CDCl3, δ): 1.40–1.95 (4H, m), 2.25–2.42 (2H, m), 2.54 (3H, s), 2.67 (1H, dd, J=13.4, 10.9Hz), 3.08–3.25 (1H, m), 3.42 (1H, dd, J=13.4, 3.6 Hz), 6.88–6.95 (1H, m), 7.05–7.45 (9H, m), 7.55–7.74 (4H, m); Mass (m/z): 554 (M+H)+.

EXAMPLE 43

The following compounds described in (1) to (4) were obtained in a similar manner to that of Example 42.

(1) 5-{[2-(4,5-Diphenyloxazol-2-yl)-2-cyclohexen-1-yl]methyl}-2-methylphenyl trifluoromethanesulfonate IR (neat): 3060, 2935, 2863, 1506, 1446, 1419, 1250, 1213, 1142, 1074 cm−1; NMR (CDCl3, δ): 1.45–1.85 (4H, m), 2.08–2.46 (2H, m), 2.33 (3H, s), 2.56 (1H, dd, J=13.3, 10.4Hz), 3.05–3.19 (1H, m), 3.22–3.35 (1H, m), 6.87–6.97 (1H, m), 7.15–7.44 (9H, m), 7.55–7.75 (4H, m); Mass (m/z): 554 (M+H)+.

(2) 3-{[2-(4,5-Diphenyloxazol-2-yl)-2-cyclohexen-1-yl]methyl}-5-methylphenyl trifluoromethanesulfonate IR (neat): 3059, 2935, 2864, 1620, 1585, 1533, 1446, 1421, 1240, 1213, 1142 cm−1; NMR (CDCl3, δ): 1.40–1.90 (4H, m), 2.08–2.40 (2H, m), 2.36 (3H, s), 2.54 (1H, dd, J=13.2, 10.3 Hz), 3.05–3.35 (2H, m), 6.85–6.95 (2H, m), 7.08 (1H, s), 7.19 (1H, s), 7.23–7.47 (6H, m), 7.57–7.77 (4H, m); Mass (m/z): 554 (M+H)+.

(3) 3-{[2-(4,5-Diphenyloxazol-2-yl)-2-cyclohexen-1-yl]methyl}-4-methylphenyl trifluoromethanesulfonate IR (neat): 3055, 2937, 2866, 1535, 1491, 1446, 1423, 1250, 1213, 1142 cm−1;

NMR (CDCl3, δ): 1.40–1.93 (4H, m), 2.18–2.50 (2H, m), 2.51 (3H, s), 2.63 (1H, dd, J=13.3, 11.0 Hz), 3.08–3.25 (1H, m), 3.35 (1H, dd, J=13.3, 3.7 Hz), 6.93 (1H, dd, J=3.8, 3.8 Hz), 6.99 (1H, dd, J=8.4, 2.7 Hz), 7.15–7.23 (2H, m), 7.23–7.47 (6H, m), 7.5–7.77 (4H, m); Mass (m/z): 554 (M+H)+.

(4) 2-{[2-(4,5-Diphenyloxazol-2-yl)-2-cyclohexen-1-yl]methyl}phenyl trifluoromethanesulfonate IR (neat): 3059, 2937, 2866, 1533, 1487, 1448, 1419, 1248, 1215, 1140 cm$^{-1}$; NMR (CDCl$_3$, δ): 1.40–2.00 (4H, m), 2.10–2.50 (2H, m), 2.94 (1H, dd, J=14.5, 10.7 Hz), 3.14–3.34 (2H, m), 6.87–6.98 (1H, m), 7.10–7.78 (14H, m); Mass (m/z): 540 (M+H)$^+$.

EXAMPLE 44

A mixture of 3-{[2-(4,5-diphenyloxazol-2-yl)-2-cyclohexen-1-yl]methyl}-2-methylphenyl trifluoromethanesulfonate (955 mg), palladium(II) acetate (117 mg), 1,3-bis(diphenylphosphino)propane (214 mg), triethylamine (0.72 ml), and MeOH (6 ml) in DMF (12 ml) was purged for 30 minutes with carbon monoxide. The mixture was stirred under carbon monoxide atmosphere at 95° C. for 1 hour. After cooling to room temperature, the reaction mixture was diluted with EtOAc, washed with water, 1N HCl, water, saturated sodium hydrogen carbonate, water, and brine, dried over magnesium sulfate, evaporated in vacuo. The residue was purified by silica gel column chromatography (hexane-EtOAc 13:1) to give methyl 3-{[2-(4,5-diphenyloxazol-2-yl)-2-cyclohexen-1-yl]methyl}-2-methylbenzoate (226.3 mg) as an amorphous solid.

IR (KBr): 3064, 2937, 2862, 1722, 1537, 1448, 1257 cm$^{-1}$; NMR (CDCl$_3$, δ): 1.38–2.00 (4H, m), 2.10–2.50 (2H, m), 2.57–2.75 (1H, m), 2.73 (3H, s), 3.10–3.30 (1H, m), 3.43 (1H, dd, J=13.6, 4.1 Hz), 3.88 (3H, s), 6.91 (1H, dd, J=3.9, 3.9 Hz), 7.13 (1H, dd, J=7.6, 7.6 Hz), 7.25–7.43 (7H, m), 7.55–7.75 (5H, m); Mass (m/z): 464 (M+H)$^+$.

EXAMPLE 45

The following compounds described in (1) to (4) were obtained in a similar manner to that of Example 44.

(1) Methyl 5-{[2-(4,5-diphenyloxazol-2-yl)-2-cyclohexen-1-yl]methyl}-2-methylbenzoate IR (KBr): 3055, 2933, 2860, 1722, 1536, 1500, 1444, 1290, 1259 cm$^{-1}$; NMR (CDCl$_3$, δ): 1.40–1.90 (4H, m), 2.10–2.38 (2H, m), 2.54 (3H, s), 2.58 (1H, dd, J=13.2, 10.3 Hz), 3.07–3.35 (2H, m), 3.85 (3H, s), 6.88–6.97 (1H, m), 7.16 (1H, d, J=7.8 Hz), 7.22–7.43 (7H, m), 7.55–7.75 (4H, m), 7.87 (1H, d, J=0.9 Hz); Mass (m/z): 464 (M+H)$^+$.

(2) Methyl 3-{[2-(4,5-diphenyloxazol-2-yl)-2-cyclohexen-1-yl]methyl}-5-methylbenzoate IR (KBr): 3059, 2933, 2860, 1720, 1604, 1537, 1444, 1309, 1219 cm$^{-1}$; NMR (CDCl$_3$, δ): 1.35–1.95 (4H, m), 2.10–2.45 (2H, m), 2.35 (3H, s), 2.58 (1H, dd, J=12.7, 9.5 Hz), 3.10–3.33 (2H, m), 3.87 (3H, s), 6.92 (1H, dd, J=3.9, 3.9 Hz), 7.25–7.46 (7H, m), 7.58–7.77 (5H, m), 7.79 (1H, s); Mass (m/z): 464 (M+H)$^+$.

(3) Methyl 3-{[2-(4,5-diphenyloxazol-2-yl)-2-cyclohexen-1-yl]methyl}-4-methylbenzoate IR (KBr): 3045, 2935, 2862, 1718, 1606, 1537, 1439, 1296, 1267 cm$^{-1}$; NMR (CDCl$_3$, δ): 1.42–2.04 (4H, m), 2.20–2.45 (2H, m), 2.56 (3H, s), 2.67 (1H, dd, J=13.2, 10.3 Hz), 3.10–3.30 (1H, m), 3.35 (1H, dd, J=13.2, 4.2 Hz), 3.85 (3H, s), 6.83–6.93 (1H, m), 7.18 (1H, d, J=8.0 Hz), 7.21–7.45 (6H, m), 7.54–7.78 (5H, m), 7.91 (1H, d, 10 J=1.7 Hz); Mass (m/z): 464 (M+H)$^+$.

(4) Methyl 2-{[2-(4,5-diphenyloxazol-2-yl)-2-cyclohexen-1-yl]methyl}benzoate

IR (neat): 3057, 2935, 2862, 1722, 1603, 1533, 1487, 1446, 1261 cm$^{-1}$; NMR (CDCl$_3$, δ): 1.40–2.00 (4H, m), 2.10–2.50 (2H, m), 3.20–3.43 (3H, m), 3.86 (3H, s), 6.88–6.98 (1H, m), 7.10–7.80 (14H, m); Mass (m/z): 450 (M+H)$^+$.

EXAMPLE 46

A mixture of 3-{[2-(4,5-diphenyloxazol-2-yl)-2-cyclopenten-1-yl]methyl}phenyl trifluoromethanesulfonate (400 mg), 3-methoxycarbonylphenylboronic acid (177 mg), triethylamine (0.318 ml), and tetrakis(triphenylphosphine)palladium(0) (64 mg) in DMF (8 ml) was stirred at 100° C. for 3.5 hours. After cooling to room temperature, the reaction mixture was diluted with EtOAc, washed with water, 1N HCl, water, saturated sodium hydrogen carbonate, water, and brine, dried over magnesium sulfate, evaporated in vacuo. The residue was purified by silica gel column chromatography (hexane-EtOAc 10:1) to give methyl 3'-{[2-(4,5-diphenyloxazol-2-yl)-2-cyclopenten-1-yl]methyl}biphenyl-3-carboxylate (264.6 mg) as an oil.

IR (neat): 3057, 2949, 2843, 1724, 1603, 1441, 1308, 1252 cm$^{-1}$; NMR (CDCl$_3$, δ): 1.80–2.20 (2H, m), 2.39–2.54 (2H, m), 2.75 (1H, dd, J=13.4, 9.1 Hz), 3.45 (1H, dd, J=13.4, 4.3 Hz), 3.52–3.72 (1H, m), 3.93 (3H, s), 6.68–6.76 (1H, m), 7.23–7.78 (16H, m), 7.95–8.05 (1H, m), 8.23–8.30 (1H, m); Mass (m/z): 512 (M+H)$^+$.

EXAMPLE 47

To a solution of methyl 3-{[2-(4,5-diphenyloxazol-2-yl)-2-cyclohexen-1-yl]methyl}-2-methylbenzoate (119 mg) in EtOAc (8 ″1) and MeOH (10 ml) was added 10% Pd/C (wet) (60 mg) and the mixture was stirred under hydrogen atmosphere at 3 atm at room temperature for 18 hours. The catalyst was removed by filtration and the filtrate was evaporated to give methyl 3-{[2-(4,5-diphenyloxazol-2-yl)-1-cyclohexyl]methyl}-2-methyl-benzoate (115.3 mg) as an amorphous solid.

IR (KBr):3064, 2929, 2854, 1720, 1560, 1502, 1446, 1261 cm$^{-1}$; NMR (CDCl$_3$, δ): 1.00–2.90 and 3.18–3.33 (total 12H, each m), 2.41 and 2.42 (total 3H, each s), 3.84 and 3.86 (total 3H, each s), 6.98–7.73 (13H, m); Mass (m/z): 466 (M+H)$^+$.

EXAMPLE 48

The following compounds described in (1) to (3) were obtained in a similar manner to that of Example 47.
(1) Methyl 5-{[2-(4,5-diphenyloxazol-2-yl)-1-cyclohexyl]methyl}-2-methylbenzoate IR (neat):3057, 2929, 2854, 1722, 1604, 1563, 1500, 1446, 1261, 1200 cm$^{-1}$; NMR (CDCl$_3$, δ): 1.00–2.80 and 3.15–3.28 (total 12H, each m), 2.45 and 2.50 (total 3H, each s), 3.77 and 3.79 (total 3H, each s), 7.00–7.73 (13H, m); Mass (m/z): 466 (M+H)$^+$.

(2) Methyl 3-{[2-(4,5-diphenyloxazol-2-yl)-1-cyclohexyl]methyl}-5-methylbenzoate IR (neat): 3057, 2929, 2854, 1722, 1604, 1564, 1446, 1309, 1219 cm$^{-1}$; NMR (CDCl$_3$, δ): 1.05–2.80 and 3.15–3.26 (total 12H, each m), 2.21 and 2.27 (total 3H, each s), 3.79 and 3.82 (total 3H, each s), 7.10 (1H, br s), 7.20–7.73 (12H, m); Mass (m/z): 466 (M+H)$^+$.

(3) Methyl 3-{[2-(4,5-diphenyloxazol-2-yl)-1-cyclohexyl]methyl}-4-methylbenzoate IR (neat): 3057, 2931, 2856, 1720, 1606, 1566, 1444, 1296, 1269 cm$^{-1}$; NMR (CDCl$_3$, δ): 1.03–2.85 and 3.18–3.33 (total 12H, each m), 2.27 and 2.28 (total 3H, each s), 3.79 and 3.80 (total 3H, each s), 7.03–7.17 (1H, m), 7.22–7.88 (12H, m); Mass (m/z): 466 (M+H)$^+$.

EXAMPLE 49

A mixture of methyl 3'-{[2-(4,5-diphenyloxazol-2-yl)-2-cyclopenten-1-yl]methyl}biphenyl-3-carboxylate (204 mg)

and 10% Pd/C (wet) (50 mg) in EtOAc (3 ml) and MeOH (3 ml) was stirred under hydrogen atmosphere at room temperature for 14 hours. The catalyst was removed by filtration and the filtrate was evaporated in vacuo. The residue was purified by silica gel column chromatography (hexane-EtOAc 12:1 to 6:1) to give methyl 3'-{[2-(4,5-diphenyloxazol-2-yl)-1-cyclopentyl]methyl}biphenyl-3-carboxylate (172.1 mg) as an oil.

IR (neat): 3057, 2951, 2871, 1724, 1604, 2566, 1442, 1308, 1252 cm$^{-1}$; NMR (CDCl$_3$, δ): 1.38–2.38 (6H, m), 2.41–3.10 and 3.44–3.48 (total 4H, each m), 3.92 and 3.93 (total 3H, each s), 7.10–7.73 (16H, m), 7.92–8.02 (1H, m), 8.14–8.23 (1H, m); Mass (m/z): 514 (M+H)$^+$.

EXAMPLE 50

To a solution of methyl 3-{[2-(4,5-diphenyloxazol-2-yl)-2-cyclohexen-1-yl]methyl}-2-methylbenzoate (100 mg) in MeOH-1,4-dioxane (1:2, 4.5 ml) was added iN NaOH solution (1.0 ml) and the mixture was stirred at 70° C. for 1 hour. After cooling, the mixture was acidified with iN HCl and extracted with EtOAc. The organic layer was washed with water and brine, dried over magnesium sulfate, evaporated in vacuo to give 3-{[2-(4,5-diphenyloxazol-2-yl)-2-cyclohexen-1-yl]-methyl}-2-methylbenzoic acid (97.0 mg) as a solid.

IR (KBr): 3059, 2935, 2860, 2646, 1685, 1587, 1539, 1446, 1302, 1269 cm$^{-1}$; NMR (DMSO-d$_6$, δ): 1.30–2.05 (4H, m), 2.05–2.50 (2H, m), 2.55–2.75 (1H, m), 2.65 (3H, s), 2.93–3.17 (1H, m), 3.18–3.45 (1H, m), 6.85–6.95 (1H, m), 7.19 (1H, dd, J=7.5, 7.5 Hz), 7.30–7.70 (12H, m), 12.80 (1H, br); Mass (m/z): 450 (M+H)$^+$.

EXAMPLE 51

The following compounds described in (1) to (9) were obtained in a similar manner to that of Example 50.

(1) 3-{[2-(4,5-Diphenyloxazol-2-yl)-1-cyclohexyl]methyl}-2-methylbenzoic acid

IR (KBr): 3059, 2929, 2854, 2642, 1689, 1560, 1446, 1240 cm$^{-1}$; NMR (CDCl$_3$, δ): 1.00–2.95 and 3.20–3.33 (total 12H, each m), 2.50 (3H, s), 7.00–7.80 (13H, m); Mass (m/z): 452 (M+H)$^+$.

(2) 5-{[2-(4,5-Diphenyloxazol-2-yl)-2-cyclohexen-1-yl]-methyl}-2-methylbenzoic acid IR (KBr): 3026, 2931, 2860, 2654, 1689, 1604, 1570, 1533, 1500, 1446, 1267 cm$^{-1}$; NMR (DMSO-d$_6$, δ): 1.35–1.95 (4H, m), 2.06–2.70 (3H, m), 2.47 (3H, s), 2.90–3.30 (2H, m), 6.83–6.97 (1H, m), 7.22 (1H, d, J=7.8 Hz), 7.27–7.74 (11H, m), 8.00 (1H, s), 12.79 (1H, br); Mass (m/z): 450 (M+H)$^+$.

(3) 5-{[2-(4,5-Diphenyloxazol-2-yl)-1-cyclohexyl]methyl}-2-methylbenzoic acid

IR (KBr): 3057, 2927, 2854, 1687, 1606, 1562, 1500, 1446, 1254 cm$^{-1}$; NMR (CDCl$_3$, δ): 1.00–2.87 and 3.17–3.30 (total 12H, each m), 2.52 and 2.57 (total 3H, each s), 7.03–7.90 (13H, m). Mass (m/z): 452 (M+H)$^+$.

(4) 3-{[2-(4,5-Diphenyloxazol-2-yl)-2-cyclohexen-1-yl]-methyl}-5-methylbenzoic acid IR (KBr): 3049, 2933, 2860, 1682, 1603, 1529, 1446, 1309, 1244 cm$^{-1}$; NMR (DMSO-d$_6$, δ): 1.30–1.98 (4H, m), 2.08–2.70 (3H, m), 2.32 (3H, s), 2.93–3.25 (2H, m), 6.85–6.95 (1H, m), 7.30–7.73 (12H, m), 7.77 (1H, s), 12.84 (1H, br); Mass (m/z): 450 (M+H)$^+$.

(5) 3-{[2-(4,5-Diphenyloxazol-2-yl)-1-cyclohexyl]methyl}-5-methylbenzoic acid

IR (KBr): 3059, 2927, 2854, 1687, 1604, 1560, 1446, 1308, 1240 cm$^{-1}$; NMR (CDCl$_3$, δ): 1.00–2.85 and 3.18–3.32 (total 12H, each m), 2.24 and 2.30 (total 3H, each s), 7.16 (1H, br s), 7.20–7.75 (12H, m); Mass (m/z): 452 (M+H)$^+$.

(6) 3-{[2-(4,5-Diphenyloxazol-2-yl)-2-cyclohexen-1-yl]-methyl}-4-methylbenzoic acid IR (KBr): 3028, 2931, 2864, 1689, 1610, 1576, 1537, 1446, 1425, 1309, 1279 cm$^{-1}$; NMR (DMSO-d$_6$, δ): 1.40–2.00 (4H, m), 2.10–2.43 (2H, m), 2.51 (3H, s), 2.60–2.78 (1H, m), 3.00–3.40 (2H, m), 6.88–6.97 (1H, m), 7.25 (1H, d, J=7.9 Hz), 7.33–7.74 (11H, m), 7.87 (1H, s); Mass (m/z): 450 (M+H)$^+$.

(7) 3-{[2-(4,5-Diphenyloxazol-2-yl)-1-cyclohexyl]methyl}-4-methylbenzoic acid

IR (KBr): 3056, 2929, 2856, 1687, 1608, 1560, 1446, 1273, 1242 cm$^{-1}$; NMR (CDCl$_3$, δ): 1.05–2.88 and 3.18–3.33 (total 12H, each m), 2.29 and 2.30 (total 3H, each s), 7.07–7.20 (1H, m), 7.20–7.95 (12H, m); Mass (m/z): 452 (M+H)$^+$.

(8) 3'-{[2-(4,5-Diphenyloxazol-2-yl)-2-cyclopenten-1-yl]-methyl}biphenyl-3-carboxylic acid IR (KBr): 3055, 2929, 1691, 1603, 1543, 1444, 1306, 1240 cm$^{-1}$; NMR (DMSO-d$_6$, δ): 1.60–2.20 (2H, m), 2.35–2.58 (2H, m), 2.65–2.83 (1H, m), 3.10–3.85 (2H, m), 6.70–6.77 (1H, m), 7.20–7.98 (17H, m), 8.18 (1H, s); Mass (m/z): 498 (M+H)$^+$.

(9) 3'-{[2-(4,5-Diphenyloxazol-2-yl)-1-cyclopentyl]methyl}-biphenyl-3-carboxylic acid IR (KBr): 3055, 2952, 2870, 1691, 1603, 1560, 1444, 1306, 1240 cm$^{-1}$; NMR (DMSO-d$_6$, δ): 1.35–2.25 (6H, m), 2.50–3.60 (4H, m), 7.11–7.58 (15H, m), 7.68–7.80 (1H, m), 7.80–7.93 (1H, m), 8.07–8.17 (1H, m); Mass (m/z): 500 (M+H)$^+$.

EXAMPLE 52

To a solution of methyl 2-{[2-(4,5-diphenyloxazol-2-yl)-2-cyclohexen-1-yl]methyl}benzoate (37 mg) in MeOH-1,4-dioxane (1:1, 3 ml) was added iN NaOH solution (1.0 ml) at 5° C. and the mixture was stirred at 80° C. for 3 hours. After cooling, the mixture was acidified with iN HCl and extracted with EtOAc. The organic layer was washed with water and brine, dried over magnesium sulfate, evaporated in vacuo. The residue was dissolved in MeOH-1,4-dioxane (1:1, 2 ml) and 1N NaOH solution (0.0824 ml) was added thereto. The mixture was evaporated and Et$_2$ was added. The resulting solid was collected by filtration to give sodium 2-{[2-(4,5-diphenyloxazol-2-yl)-2-cyclohexen-1-yl1methyl}benzoate (19.9 mg).

IR (KBr): 3421, 3057, 2929, 1603, 1579, 1558, 1442, 1406 cm$^{-1}$; NMR (DMSO-d$_6$, δ): 1.20–2.43 (6H, m), 2.80–3.20 (2H, m), 3.55–3.73 (1H, m), 6.80–6.90 (1H, m), 6.93–7.15 (2H, m), 7.20–7.53 (8H, m), 7.55–7.70 (4H, m); Mass (m/z): 458 (M+H)$^+$.

EXAMPLE 53

To a solution of 3'-{[2-(4,5-diphenyloxazol-2-yl)-2-cyclopenten-1-yl]methyl}biphenyl-3-carboxylic acid (74 mg) and N-methylmorpholine (0.0197 ml) in THF (4 ml) was added isobutyl chloroformate (0.0232 ml) at 0° C. After stirring for 15 minutes, 28% ammonia solution (0.1 ml) was added thereto. The mixture was stirred at the same temperature for 15 minutes, then stirred at room temperature for 15 minutes. The reaction mixture was diluted with EtOAc, washed with water, 1N HCl, water, and brine, dried over magnesium sulfate, evaporated in vacuo. The residue was purified by silica gel column chromatography (CH$_2$Cl$_2$-MeOH 25:1) to give 3'-{[2-(4,5-diphenyloxazol-2-yl)-2- cyclopenten-1-yl]methyl}-biphenyl-3-carboxamide (51.8 mg) as a solid.

IR (KBr): 3375, 3182, 3060, 1647, 1587, 1523, 1444, 1406 cm$^{-1}$; NMR (DMSO-d$_6$, δ): 1.75–2.20 (2H, m), 2.35–2.55 (2H, m), 2.74 (1H, dd, J=13.3, 9.2 Hz), 3.25–3.43 (2H, m), 6.70–6.78 (1H, m), 7.20–7.70 (16H, m), 7.70–7.90 (2H, m), 8.05–8.20 (2H, m); Mass (m/z): 497 (M+H)$^+$.

EXAMPLE 54

The following compound was obtained in a similar manner to that of Example 53.

3'-{[2-(4,5-Diphenyloxazol-2-yl)-1-cyclopentyl]methyl}-biphenyl-3-carboxamide

IR (neat): 3348, 3194, 3059, 2958, 2871, 1666, 1603 1577, 1446, 1408, 1383 cm$^{-1}$; NMR (CDCl$_3$, δ): 1.40–3.15 and 3.40–3.58 (total 10H, each m), 7.10–7.68 (16H, m), 7.70–7.80 (1H, m), 7.90–7.95 (1H, m); Mass (m/z): 499 (M+H)$^+$.

EXAMPLE 55

To a solution of 4-bromoanisole (1.00 g) in tetrahydrofuran (4 ml), n-butyllithium hexane solution (1.56M, 3.4 ml) was added at −78° C. under a flow of nitrogen. After stirring for 0.5 hour, a solution of 2-[(4,5-diphenyloxazol-2-yl) methyl]cyclohexan-1-one (1.36 g) in tetrahydrofuran (3 ml) was added below −50° C. to the reaction mixture and stirred for 0.5 hour. After usual workup, the crude product was purified by column chromatography (silica gel 50 g, eluent; hexane/ethyl acetate=9 then 4) to give 2-[(4,5-diphenyloxazol-2-yl)methyl]-1-(3-methoxyphenyl)-1-cyclohexanol (1.01 g) as a foam.

IR (film): 3420, 2935, 1604, 1581, 1484, 1446, 1288, 1249, 1160, 1056, 1047, 964, 775, 696 cm$^{-1}$; NMR (CDCl$_3$, δ): 1.3–2.0 (10H, m), 2.38–2.58 (1H, m), 2.68 (2H, d, J=6.1 Hz), 3.78 (3H, s), 6.70–6.76 (1H, m), 7.08–7.45 (9H, m), 7.49–7.63 (4H, m); Mass (m/z): 440 (M+H)$^+$, 422.

EXAMPLE 56

A mixture of 2-[(4,5-diphenyloxazol-2-yl)methyl]-1-(3-methoxyphenyl)cyclohexan-1-ol (990 mg), p-toluenesulfonic acid monohydrate (22 mg) and acetic acid (5 ml) was heated at 130° C. for 6 hours. After usual workup and purification by column chromatography (silica gel, 45 g, eluent; hexane/ethyl acetate=9), 1-(4,5-diphenyloxazol-2-yl)methyl]-2-(3- methoxyphenyl)-2-cyclohexene (551 mg) as a pasty solid.

IR (film): 2931, 1602, 1574, 1487, 1454, 1429, 1286, 1205, 1171, 1057, 962, 764, 694 cm$^{-1}$; NMR (CDCl$_3$, δ): 1.63–1.80 (2H, m), 1.80–1.92 (2H, m), 2.15–2.29 (2H, m), 2.75 (1H, dd, J=9.5, 14.9 Hz), 2.93 (1H, dd, J=5.0, 14.9 Hz), 3.32–3.50 (1H, m), 3.73 (3H, s), 6.00–6.04 (1H, m), 6.68–6.76 (1H, m), 6.88–6.99 (2H, m), 7.14 (1H, t, J=7.9 Hz), 7.28–7.42 (6H, m), 7.48–7.62 (4H, m); Mass (m/z): 422 (M+H)$^+$.

EXAMPLE 57

The following compounds described in (1) to (2) were prepared in a similar manner to that of Example 38.
(1) A mixture of 3-(4,5-diphenyloxazol-2-yl)-1-(3-methoxybenzyl)-2-cyclohexene and 3-(4,5-diphenyloxazol-2-yl)-1-(3-methoxybenzyl)-3-cyclohexene IR (film): 2929, 1601, 1585, 1487, 1448, 1261, 1153, 1061, 1043, 964, 766, 694 cm$^{-1}$; NMR (CDCl$_3$, δ): 1.3–1.4 (1H, m), 1.7–2.1 (2H, m), 2.1–2.4 (2H, m), 2.50–2.92 (4H, m), 3.81 (3H, s), 6.72–6.96 (4H, m), 7.18–7.45 (7H, m), 7.54–7.72 (4H, m); Mass (m/z): 422 (M+H)$^+$.
(2) A mixture of 3-(4,5-diphenyloxazol-2-yl)-1-(3-methoxyphenyl)-2-cyclohexene and 3-(4,5-diphenyloxazol-2-yl)-1-(3-methoxyphenyl)-3-cyclohexene

EXAMPLE 58

The following compounds described in (1) to (3) were obtained in a similar manner to that of Example 22.
(1) A mixture of methyl 3-{[3-(4,5-diphenyloxazol-2-yl)-2-cyclohexen-1-yl]methyl}benzoate and methyl 3-{[3-(4,5-diphenyloxazol-2-yl)-3-cyclohexen-1-yl]methyl}benzoate IR (film): 2929, 1722, 1537, 1446, 1284, 1203, 1107, 964, 764, 696 cm$^{-1}$; NMR (CDCl$_3$, δ): 1.3–1.5 (1H, m), 1.7–2.4 (4H, m), 2.5–2.9 (4H, m), 3.91 (3H, s), 6.78 (0.4H, br s), 6.88 (0.6H, br s), 7.30–7.48 (8H, m), 7.56–7.70 (4H, m), 7.86–7.96 (2H, m); Mass (m/z): 450 (M+H)$^+$.
(2) A mixture of methyl 3-[3-(4,5-diphenyloxazol-2-yl)-2-cyclohexen-1-yl]benzoate and methyl 3-[3-(4,5-diphenyloxazol-2-yl)-3-cyclohexen-1-yl]benzoate IR (film): 2931, 1718, 1537, 1444, 1286, 1196, 1109, 964, 756, 694 cm$^{-1}$; NMR (CDCl$_3$, δ): 1.5–2.2 (3H, m), 2.42–3.16 (4H, m), 3.92 (3H, s), 6.89 (0.4H, br s), 6.97 (0.6H, br s), 7.25–7.53 (8H, m), 7.53–7.73 (4H, m), 7.88–8.02 (2H, m); Mass (m/z): 436 (M+H)$^+$.
(3) Methyl 3-{1-[(4,5-diphenyloxazol-2-yl)methyl]-2-cyclohexen-2-yl}benzoate IR (film): 2933, 1726, 1720, 1579, 1442, 1292, 1227, 1110, 1061, 964, 762, 696 cm$^{-1}$; NMR (CDCl$_{3, δ}$): 1.67–1.82 (2H, m), 1.84–1.95 (2H, m), 2.20–2.40 (2H, m), 2.79 (1H, dd, J=8.5, 14.7 Hz), 2.92 (1H, dd, J=6.2, 14.7 Hz), 3.40–3.53 (1H, m), 3.81 (3H, s), 6.03 (1H, dt, J=0.7, 3.2 Hz), 7.21–7.40 (7H, m), 7.42–7.56 (4H, m), 7.80 (1H, d, J=7.4 Hz), 8.00 (1H, d, J=1.7 Hz); Mass (m/z): 450 (M+H)$^+$.

EXAMPLE 59

The following compounds described in (1) to (3) were prepared in a similar manner to that of Example 24.
(1) A mixture of 3-{[3-(4,5-diphenyloxazol-2-yl)-2-cyclohexen-1-yl]methyl}benzoic acid and 3-{[3-(4,5-diphenyloxazol-2-yl)-3-cyclohexen-1-yl]methyl}benzoic acid IR (KBr): 3432, 2924, 1695, 1535, 1446, 1298, 1211, 1074, 964, 764, 692 cm$^{-1}$; NMR (CDCl$_3$, δ): 1.3–1.5 (1H, m), 1.5–2.4 (4H, m), 2.5–2.9 (4H, m), 6.79 (0.4H, br s), 6.88 (0.6H, br s), 7.3–7.7 (12H, m), 7.9–8.0 (2H, m); Mass (m/z): 436 (M+H)$^+$.
(2) A mixture of 3-[3-(4,5-diphenyloxazol-2-yl)-2-cyclohexen-1-yl]benzoic acid and 3-[3-(4,5-diphenyloxazol-2-yl)-3-cyclohexen-1-yl]benzoic acid.

IR (film): 3435, 2927, 1693, 1446, 1292, 1076, 966, 764, 694 cm$^{-1}$; NMR (CDCl$_3$, δ) 1.5–2.2 (3H, m) 2.4–3.18 (4H, m), 6.90 (0.4H, br s), 6.97 (0.6H, br s), 7.3–7.74 (12H, m), 7.90–8.06 (2H, m); Mass (m/z): 422 (M+H)$^+$.
(3) 3-{1-[(4,5-Diphenyloxazol-2-yl)methyl]-2-cyclohexen-2-yl}benzoic acid IR (KBr): 3448, 2925, 1709, 1444, 1282, 1224, 1063, 760, 694 cm$^{-1}$; NMR (CDCl$_3$, δ): 1.56–1.90 (4H, m), 2.12–2.27 (2H, m), 2.78 (2H, d, J=6.5Hz), 3.3–3.46 (7H, m), 6.04 (1H, t, J=3.3 Hz), 7.3–7.6 (12H, m), 7.73 (1H, d, J=7.7 Hz), 7.92 (1H, s), 12.9 (1H, br s); Mass (m/z): 436 (M+H)$^+$.

EXAMPLE 60

The following compounds described in (1) to (6) were obtained in a similar manner to those of Example 22 and Example 24.

(1) 4-{[2-(4,5-Diphenyloxazol-2-yl)-2-cyclohepten-1-yl]-methyl}benzoic acid NMR (CDCl$_3$, δ): 1.4–2.0 (6H, m), 2.3–2.6 (2H, m), 2.98 (1H, m), 3.05 (1H, m), 3.82 (1H, m), 7.09 (1H, t, J=8.0 Hz), 7.2–8.2 (14H, m); Mass (m/z): 450 (M+H)$^+$.

(2) 4-{[3-(4,5-Diphenyloxazol-2-yl)bicyclo[2.2.1]hept-2-en-2-yl]methyl}benzoic acid IR (Nujol): 1700 cm$^{-1}$; NMR (CDCl$_3$, δ): 1.0–2.0 (6H, m), 2.82 (1H, br s), 3.62 (1H, br s), 3.70 ($^1$H, d, J=14 Hz), 4.40 (1H, d, J=14 Hz), 7.2–8.1 (14H, m); Mass (m/z): 448 (M+H)$^+$.

(3) 3-{[2-(4,5-Diphenyloxazol-2-yl)-2-cycloocten-1-yl]-methyl}benzoic acid Mass (m/z): 464 (M+H)$^+$.

(4) 4-{[2-(4,5-Diphenyloxazol-2-yl)-2-cyclopenten-1-yl]-methyl}benzoic acid

IR (Nujol): 1680 cm$^{-1}$; NMR (CDCl$_3$, δ): 1.8–2.2 (2H, m), 2.3–2.5 (2H, m), 2.72 (1H, dd, J=9, 14 Hz), 2.99 (2H, m), 3.48 (1H, dd, J=5, 15 Hz), 3.60 (1H, m), 6.71 (1H, m), 7.2–8.1 (14H, m); Mass (m/z): 422 (M+H)$^+$.

(5) 3-{{2-[4,5-Di(4-methylphenyl)oxazol-2-yl]-2-cyclohexen-1-yl}methyl}benzoic acid IR (Nujol) 1680 cm$^{-1}$; NMR (CDCl$_3$, δ): 1.5–2.4 (6H, m), 2.33 (6H, s), 2.60 (1H, m), 3.1–3.4 (2H, m), 6.90 (1H, m), 7.0–8.2 (14H, m); Mass (m/z): 464 (M+H)$^+$.

(6) 3-{[(2-(4,5-Diphenylthiazol-2-yl)-2-cyclohexen-1-yl]-methyl}benzoic acid

IR (Nujol): 1680 cm$^{-1}$; NMR (CDCl$_3$, δ): 1.3–2.8 (7H, m), 3.2–3.4 (2H, m), 6.64 (1H, m), 7.2–8.2 (14H, m); Mass (m/z): 452 (M+H)$^+$.

EXAMPLE 61

The following compounds described in (1) to (2) were obtained according to a similar manner to that of Example 29.

(1) 4-{[3-(4,5-Diphenyloxazol-2-yl)bicyclo[2.2.1]heptan-2-yl]methyl}benzoic acid; Mass (m/z): 450 (M++H)$^+$.

(2) 4-{[2-(4,5-Diphenyloxazol-2-yl)-1-cyclopentyl]methyl}-benzoic acid

IR (Nujol) 1650 cm$^{-1}$; NMR (CDCl$_3$, δ): 1.5–2.9 (9H, m), 3.48 (1H, m), 7.2–8.0 (14H, m); Mass (m/z): 423 (M+H)$^+$.

What is claimed is:

1. A compound of the formula;

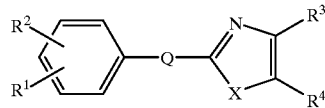

wherein $R^1$ is lower alkyl substituted with hydroxy, protected carboxy or carboxy; carboxy; protected carboxy; carbamoyl; a heterocyclic group; cyano; halo(lower)alkylsulfonyloxy; lower alkoxy substituted with hydroxy or carbamoyl; aryl substituted with carboxy, protected carboxy, carbamoyl or a heterocyclic group; or amino optionally substituted with protected carboxy or lower alkylsulfonyl, $R^2$ is hydrogen or lower alkyl, $R^3$ is aryl optionally substituted with halogen, $R^4$ is aryl optionally substituted with halogen, Q is

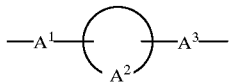

[in which —A$^1$— is a single bond or lower alkylene,

is cyclo(C$_5$–C$_9$)alkene, cyclo(C$_3$–C$_9$)alkane, bicyclo(C$_6$–C$_9$)alkene or bicyclo(C$_5$–C$_9$)alkane, and —A$^3$— is a single bond or lower alkylene], and X is O or S, and its salt.

2. A compound according to the claim 1, wherein X is O.

3. A compound according to the claim 2, wherein $R^1$ is lower alkyl substituted with carboxy; carboxy; protected carboxy; carbamoyl; a heterocyclic group; lower alkoxy substituted with carbamoyl; aryl substituted with carboxy, carbamoyl or a heterocyclic group; or amino optionally substituted with lower alkylsulfonyl.

4. A compound according to the claim 3, wherein $R^1$ is lower alkyl substituted with carboxy; carboxy; carbamoyl; tetrazolyl; lower alkoxy substituted with carbamoyl; aryl substituted with carboxy or carbamoyl, and Q is

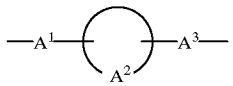

[in which —A$^1$— is methylene,

is cyclo(C$_5$–C$_7$)alkene, cyclo(C$_5$–C$_7$)alkane, bicyclo[2.2.1]heptene or bicyclo[2.2.1]heptane, and —A$^3$— is a single bond].

5. A process for production of the compound of the formula:

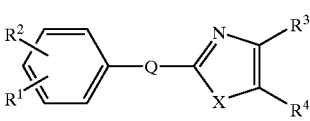

(I)

wherein $R^1$ is lower alkyl substituted with hydroxy, protected carboxy or carboxy; carboxy; protected carboxy; carbamoyl; a heterocyclic group; cyano; halo (lower)alkylsulfonyloxy; lower alkoxy substituted with hydroxy or carbamoyl; aryl substituted with carboxy, protected carboxy, carbamoyl or a heterocyclic group; or amino optionally substituted with protected carboxy or lower alkylsulfonyl, $R^2$ is hydrogen or lower alkyl,
$R^3$ is aryl optionally substituted with halogen,
$R^4$ is aryl optionally substituted with halogen,
Q is

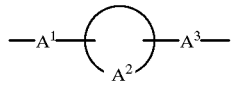

[in which —$A^1$— is a single bond or lower alkylene,

is cyclo($C_5$–$C_9$) alkene, cyclo($C_3$–$C_9$)alkane, bicyclo($C_6$–$C_9$)alkene or bicyclo($C_5$–$C_9$)alkane, and —$A^3$— is a single bond or lower alkylene), and
X is O, or S,
or its salt, which comprises,
(1) dehydrating a compound of the formula:

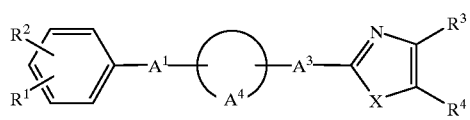
(II-1)

or its salt, to give a compound of the formula:

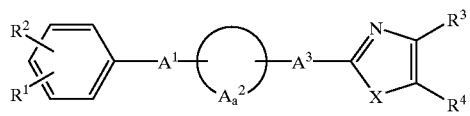
(I-1)

or its salt, in the above formulas,
$R^1$, $R^2$, $R^3$, $R^4$, —$A^1$—, —$A^3$— and X are each as defined above,

is cyclo($C_5$–$C_9$)alkene or bicyclo($C_6$–$C_9$)alkene, and,

is cyclo($C_5$–$C_9$)alkane or bicyclo($C_6$–$C_9$)alkane, each of which is substituted with hydroxy,
(2) reducing the compound of the formula (I-1) defined above, or its salt, to give a compound of the formula:

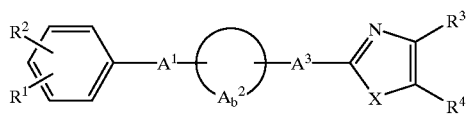
(I-2)

or its salt, in the above formula, $R^1$, $R^2$, $R^3$, $R^4$, —$A^1$—, —$A^3$— and X are each as defined above, and

is cyclo($C_5$–$C_9$)alkane or bicyclo($C_6$–$C_9$)alkane,
(3) subjecting a compound of the formula:

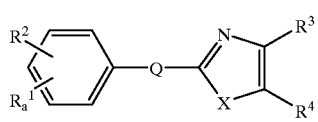
(I-3)

or its salt, to (a) a cleavage of ether bond and (b) a halo(lower)alkylsulfonylation, to give a compound of the formula:

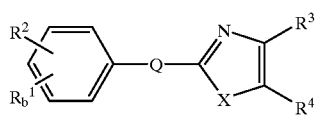
(I-4)

or its salt, in the above formulas,
$R^2$, $R^3$, $R^4$, Q and X are each as defined above,
$R_a^1$ is lower alkoxy, and
$R_b^1$ is halo(lower)alkylsulfonyloxy,
(4) subjecting the compound of the formula (I-4) defined above, or its salt, to Pd-catalyzed carbonylation, to give a compound of the formula:

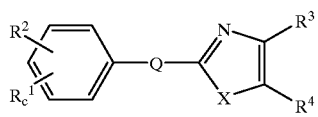
(I-5)

or its salt, in the above formula,
$R^2$, $R^3$, $R^4$, Q and X are each as defined above, and
$R_c^1$ is protected carboxy,
(5) subjecting the compound of the formula (I-5) defined above, or its salt, to deesterification, to give a compound of the formula:

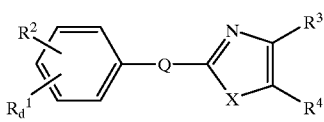

(I-6)

or its salt, in the above formula,
$R^2$, $R^3$, $R^4$, Q and X are each as defined above, and $R_d^1$ is carboxy, (6) reacting the compound of the formula (I-6) defined above, or its reactive derivative at the carboxy group, or its salt, with a compound of the formula:

$$NH_3 \qquad (III)$$

or its reactive derivative, or its salt, to give a compound of the formula:

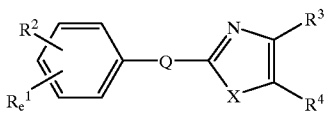

(I-7)

or its salt, in the above formulas,
$R^2$, $R^3$, $R^4$, Q and X are each as defined above, and $R_e^1$ is carbamoyl.

(7) reacting the compound of the formula (I-5) defined above, or its salt, with the compound of the formula (III) defined above, or its salt, to give the compound of the formula (I-7) or its salt, or, (8) reacting a compound of the formula:

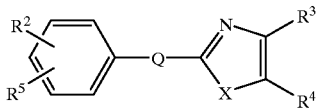

(II-2)

or its reactive derivative at carboxy group, or its salt, with the compound of the formula (III) defined above, or its reactive derivative, or its salt, to give a compound of the formula:

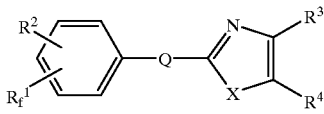

(I-8)

or its salt, in the above formula,
$R^2$, $R^3$, $R^4$, Q and X are each as defined above,
$R_f^1$ is lower alkoxy substituted with carbamoyl, and
$R^5$ is lower alkoxy substituted with carboxy or protected carboxy.

6. A Pharmaceutical composition containing a compound of the formula:

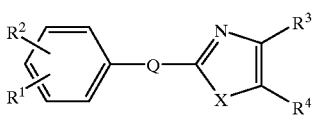

(I)

wherein $R^1$ is lower alkyl substituted with hydroxy, protected carboxy or carboxy; carboxy; protected carboxy; carbamoyl; a heterocyclic group; cyano; hydroxy; halo(lower)alkylsulfonyloxy; lower alkoxy optionally substituted with hydroxy or carbamqyl; aryl substituted with carboxy, protected carboxy, carbamoyl or a heterocyclic group; or amino optionally substituted with protected carboxy or lower alkylsulfonyl, $R^2$ is hydrogen or lower alkyl, $R^3$ is aryl optionally substituted with halogen, $R^4$ is aryl tionally substituted with halogen, Q is

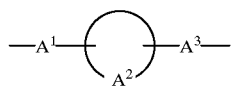

[in which —$A^1$— is a single bond or lower alkylene,

is cyclo($C_5$–$C_9$)alkene, cyclo($C_3$–$C_9$)alkane, bicyclo($C_6$–$C_9$)alkene or bicyclo($C_5$–$C_9$)alkane, and —$A^3$— is a single bond or lower alkylene], and X is O, or S, or its salt, as an active ingredient, in association with a pharmaceutically acceptable, substantially non-toxic carrier or excipient.

7. A method for treating $PGE_2$ mediated diseases which comprises administering an effective amount of a compound of claim 1 to human beings or animals.

8. The method for treating inflammatory conditions, various pains, collagen diseases, autoimmune diseases, various immunity diseases, analgesia, thrombosis, allergic disease, cancer or neurodegenerative diseases which comprises administering an effective amount of a compound of claim 1 to human beings or animals.

9. A method for agonizing or antagonizing a $PGE_2$-receptor comprising administering the compound according to claim 1 to a human being or animal in need thereof.

* * * * *